(12) United States Patent
Wu et al.

(10) Patent No.: US 8,465,461 B2
(45) Date of Patent: Jun. 18, 2013

(54) BLUNT NEEDLE SAFETY DRUG DELIVERY SYSTEM

(75) Inventors: Yongxian Wu, Wayne, NJ (US); Yun Jin, Morristown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 243 days.

(21) Appl. No.: 12/844,546

(22) Filed: Jul. 27, 2010

(65) Prior Publication Data
US 2012/0029465 A1    Feb. 2, 2012

(51) Int. Cl.
*A61M 5/00*    (2006.01)
*A61M 37/00*    (2006.01)
*A61M 5/14*    (2006.01)

(52) U.S. Cl.
USPC ........................... 604/190; 604/252; 604/6.09

(58) Field of Classification Search
USPC ................. 604/511–513, 523, 533–539, 190, 604/406, 252, 6.09
See application file for complete search history.

(56) References Cited

U.S. PATENT DOCUMENTS

| | | |
|---|---|---|
| 3,557,778 A | 1/1971 | Hughes |
| 3,570,484 A | 3/1971 | Steer |
| 4,143,853 A | 3/1979 | Abramson |
| 4,336,036 A | 6/1982 | Leeke et al. |
| 4,387,879 A | 6/1983 | Tauschinski |
| 4,485,014 A | 11/1984 | Gilroy et al. |
| 4,683,916 A | 8/1987 | Raines |
| 4,740,205 A | 4/1988 | Seltzer et al. |
| 4,838,875 A | 6/1989 | Somor |
| 5,069,225 A | 12/1991 | Okamura |
| 5,100,394 A | 3/1992 | Dudar et al. |
| 5,190,067 A | 3/1993 | Paradis et al. |
| 5,349,984 A | 9/1994 | Weinheimer et al. |
| 5,376,073 A | 12/1994 | Graves et al. |
| 5,390,898 A | 2/1995 | Smedley et al. |
| 5,437,648 A | 8/1995 | Graves et al. |

(Continued)

FOREIGN PATENT DOCUMENTS

| | | |
|---|---|---|
| EP | 1233809 B1 | 9/2004 |
| WO | WO-2006/020635 | 2/2006 |
| WO | WO-2007/089531 | 8/2007 |

OTHER PUBLICATIONS

Final Office Action in U.S. Appl. No. 12/711,641, mailed Oct. 18, 2011, 10 pgs.

(Continued)

*Primary Examiner* — Victoria P Shumate
*Assistant Examiner* — Rebecca E Eisenberg
(74) *Attorney, Agent, or Firm* — Servilla Whitney LLC

(57) ABSTRACT

Drug delivery devices having non-luer connections and adapters and adaption connectors for providing non-luer connections to drug delivery devices are provided. An exemplary drug delivery device for use with a catheter connection includes a blunt needle component with a non-luer connection and a filter component with a non-luer connection, wherein the non-luer connections of the blunt needle component and filter component are incompatible with standard luer fitting and intravenous route-accessing devices. In one or more embodiments, an adapter having a non-luer connection at one end and a luer connector is provided for use with blunt needle components and filter components wherein one of the blunt needle component and the filter component includes a luer connection and the other of the blunt needle component and the filter component includes a non-luer connection. Methods of delivering liquid medication to a catheter are also provided.

36 Claims, 25 Drawing Sheets

U.S. PATENT DOCUMENTS

| | | | |
|---|---|---|---|
| 5,437,650 | A | 8/1995 | Larkin et al. |
| 5,465,938 | A | 11/1995 | Werge et al. |
| 5,484,421 | A | 1/1996 | Smocer |
| 5,496,274 | A | 3/1996 | Graves et al. |
| 5,509,911 | A | 4/1996 | Cottone, Sr. et al. |
| 5,520,665 | A | 5/1996 | Fleetwood |
| 5,535,785 | A | 7/1996 | Werge et al. |
| 5,573,516 | A | 11/1996 | Tyner |
| 5,584,314 | A | 12/1996 | Bron |
| 5,616,133 | A | 4/1997 | Cardenas |
| 5,616,136 | A | 4/1997 | Shillington |
| 5,749,861 | A | 5/1998 | Guala et al. |
| 5,755,709 | A | 5/1998 | Cuppy |
| 5,775,671 | A | 7/1998 | Cote, Sr. |
| 5,817,063 | A | 10/1998 | Turnbull |
| 5,827,429 | A | 10/1998 | Ruschke et al. |
| 5,968,020 | A | 10/1999 | Saito |
| 6,050,978 | A | 4/2000 | Orr et al. |
| 6,096,024 | A | 8/2000 | Graves et al. |
| 6,273,870 | B1 | 8/2001 | Garvin |
| 6,402,207 | B1 | 6/2002 | Segal et al. |
| 6,428,514 | B1 | 8/2002 | Goebel et al. |
| 6,500,153 | B1 | 12/2002 | Sheppard et al. |
| 6,544,235 | B2 | 4/2003 | Motisi et al. |
| 6,605,076 | B1 | 8/2003 | Jepson et al. |
| 6,612,624 | B1 | 9/2003 | Segal et al. |
| 6,988,510 | B2 | 1/2006 | Enerson |
| 7,040,598 | B2 | 5/2006 | Raybuck |
| 7,137,654 | B2 | 11/2006 | Segal et al. |
| 7,306,566 | B2 | 12/2007 | Raybuck |
| 7,651,481 | B2 | 1/2010 | Raybuck |
| 2003/0018301 | A1 | 1/2003 | Sheppard et al. |
| 2004/0201216 | A1 | 10/2004 | Segal et al. |
| 2005/0087715 | A1 | 4/2005 | Doyle |
| 2006/0027270 | A1 | 2/2006 | Truitt et al. |
| 2006/0033331 | A1 | 2/2006 | Ziman |
| 2006/0237065 | A1 | 10/2006 | Enerson |
| 2007/0016161 | A1 | 1/2007 | Costa et al. |
| 2007/0179454 | A1 | 8/2007 | Ziman et al. |
| 2007/0260195 | A1 | 11/2007 | Bartholomew et al. |
| 2008/0045929 | A1 | 2/2008 | Birnbach |
| 2008/0058702 | A1 | 3/2008 | Arndt et al. |
| 2008/0103486 | A1 | 5/2008 | Owens |
| 2008/0139950 | A1 | 6/2008 | Molnar et al. |
| 2008/0140020 | A1 | 6/2008 | Shirley |
| 2008/0140055 | A1 | 6/2008 | Shirley |
| 2008/0312640 | A1 | 12/2008 | Grant |
| 2008/0318456 | A1 | 12/2008 | Yow et al. |
| 2008/0319422 | A1 | 12/2008 | Cardenas |
| 2009/0099552 | A1 | 4/2009 | Levy et al. |
| 2009/0187166 | A1 | 7/2009 | Young |
| 2009/0318456 | A1 | 12/2009 | Herdewijn et al. |
| 2010/0286558 | A1 | 11/2010 | Schraga |
| 2011/0208160 | A1* | 8/2011 | Wu et al. ............ 604/512 |

OTHER PUBLICATIONS

PCT International Search Report & Written Opinion in PCT/US2011/045281, mailed Apr. 19, 2012, 23 pgs.

Correspondence, *British Journal of Anaesthesia* 86(6) 2001, 896-904.

Anderson, MD, Ronald A. "Letter to the Editor: Infallible Measures Needed to Prevent Errors in the Administration of Chemotherapeutic Agents", *Medical and Pediatric Oncology* 32 1999, 401-402.

Katz, Leon "Inadvertent Misconnection of Medical Tubing: Protective Incompatibility", *Health and Welfare* Canada, Ottawa 1986, 2517-2518.

Lanigan, "Correspondence", *Anesthesia*, 56 2001 , 585-610.

Stabile, M. "Medical Administration in Anesthesia", *Anesthesia Patient Safety Foundation Newsletter*, vol. 22, No. 3, (2007) 6 pgs.

Toft, Prof., Brian "External Inquiry into the adverse incident that occurred at Queen's Medical Centre, Nottingham", *Department of Health* Jan. 4, 2001, 70 pgs.

Woods, Prof., Kent W. "The Prevention of Intrathecal Medication Errors—A report to the Chief Medical Officer", *Department of Healt* Apr. 2001, 20 pgs.

Non-Final Office Action in U.S. Appl. No. 12/711,805, mailed Apr. 11, 2011, 15 pgs.

Non-Final Office Action in U.S. Appl. No. 12/711,641, mailed Jun. 23, 2011, 19 pgs.

Sheppard, Ian et al., "Medication Safety Alerts", *The Canadian Journal of Hospital Pharmacy*, vol. 57, No. 3 Jun. 2004, 4.

Final Office Action in U.S. Appl. No. 12/711,805, mailed Oct. 12, 2011, 15 pgs.

Non-Final Office Action in U.S. Appl. No. 12/711,641, mailed Oct. 10, 2012, 18 pgs.

\* cited by examiner

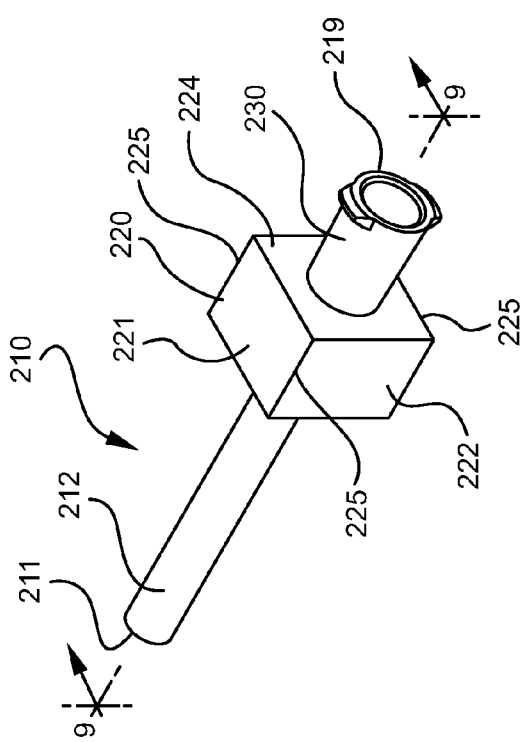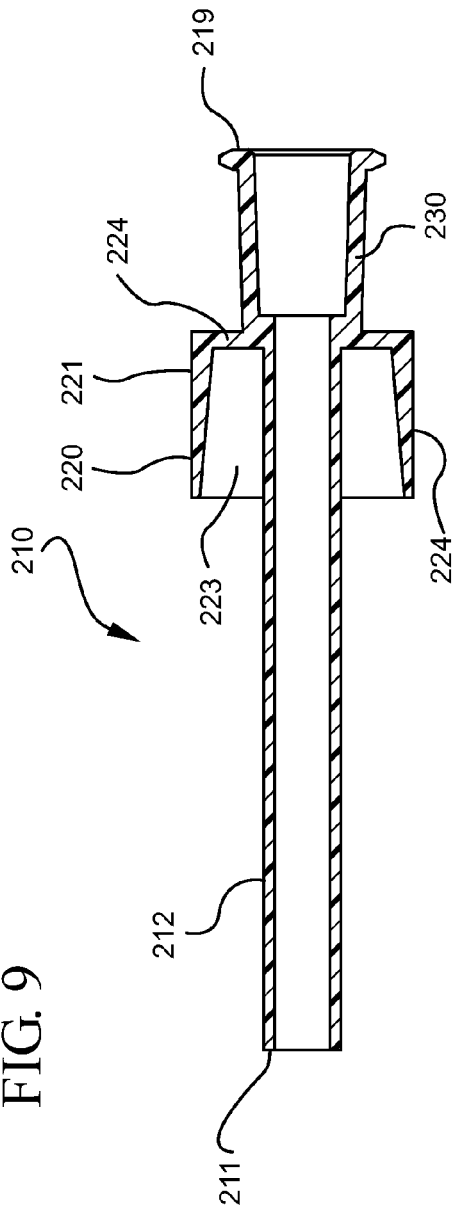

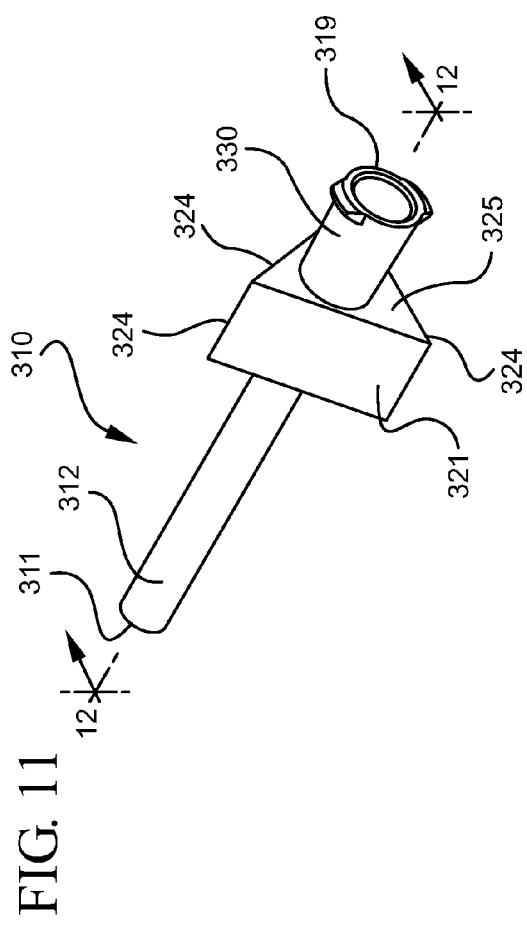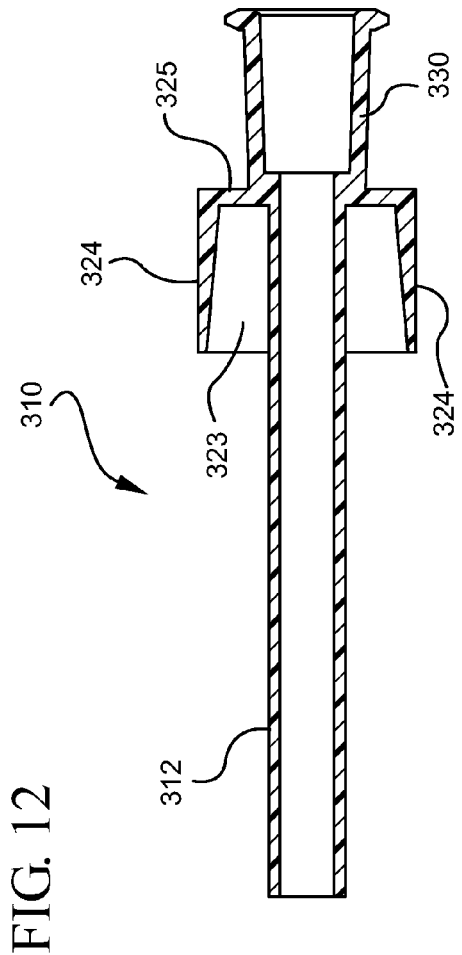

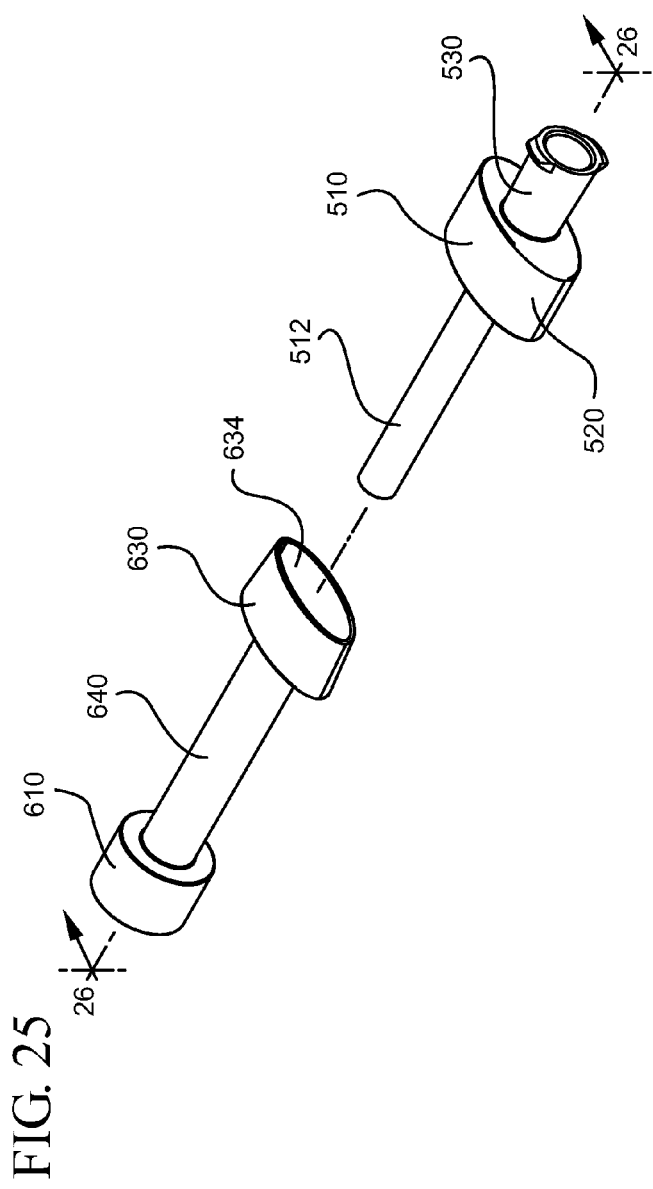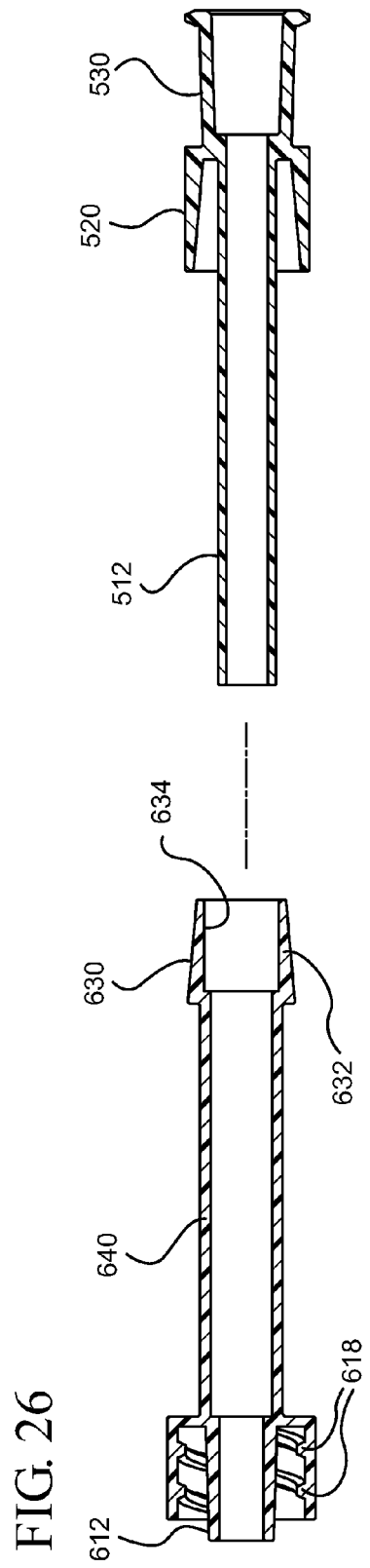
FIG. 25
FIG. 26

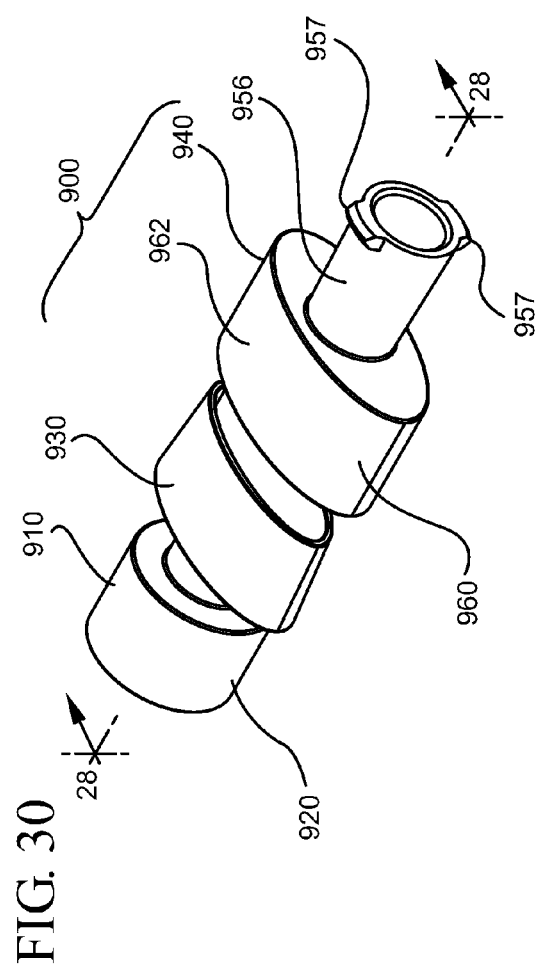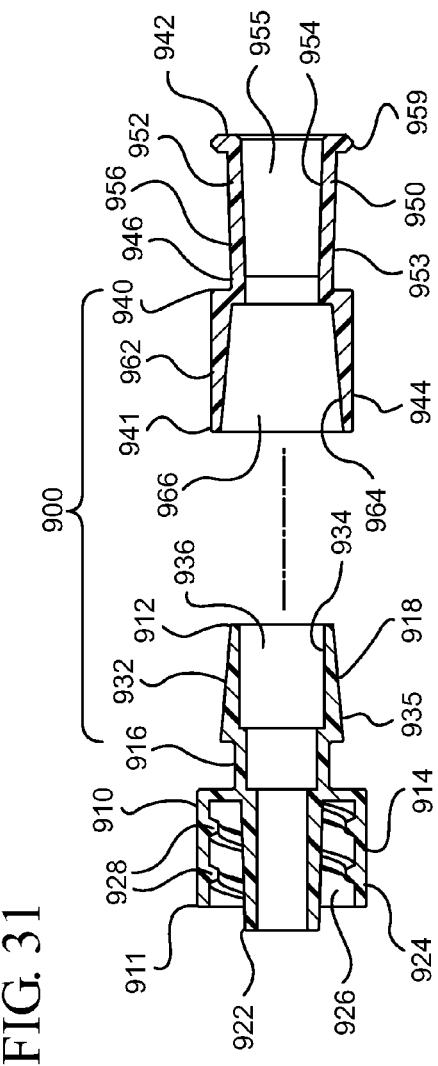

BLUNT NEEDLE SAFETY DRUG DELIVERY SYSTEM

TECHNICAL FIELD

Aspects of the present invention relate to drug delivery systems that prevent administration of medication to incorrect routs and methods of using the drug delivery systems.

BACKGROUND

Drug delivery devices typically share a common ISO standard luer connection, including intravascular, anesthesia and enteral delivery devices. Misconnections of these routes are possible and will cause medication error. The consequences of such errors may be adverse or even fatal.

Previous attempts at reducing errors in drug delivery include the use of labels or color coded devices to differentiate specific route-accessing devices (e.g., catheter connectors) and drug-containing devices or containers for retaining medication (e.g., syringe barrels). Studies have shown that clinicians tend to ignore these labels and color codes.

In addition, the number of components in some drug delivery systems that must be connected and disconnected can be time consuming and may cause confusion and/or misconnection. Commercial continuous anesthesia procedure trays are an example of a drug delivery system that includes components which must be connected and disconnected and can include a glass ampoule containing anesthesia drug, stainless steel sharp hypodermic needle and/or filter needle for withdrawing the drug, epidural filter, and catheter connectors.

Other attempts to eliminate wrong-route medication errors incorporate check valves into one or more components, however, check valves often require complicated actuation mechanisms, which may cause poor functional reliability. In addition, such devices incorporating a check valve are reliant on air and/or liquid pressure and, therefore, variations in flow rate, part dimensions, material dimension stability or surface tension may cause malfunction of the check valve. In addition, check valves are typically made from rubber, which can be difficult to machine and normally costs more than plastic. The assembly of check valves within the dispensing connector may be complicated and could require manual assembly. Moreover, the complicated structure of devices that incorporate check valves may also potentially cause infection due to the large surface area, moving parts and parts made from different materials that may cause bacterial growth.

Accordingly, there is a need for a drug delivery connector that can effectively eliminate all wrong-route medication error possibilities for use in a variety of drug delivery procedures with standard syringes and other drug-containing devices. Further, there is a need for a drug delivery connector that permits normal aspiration of medication into a container and air priming, while providing a valve that prevents leakage of the aspirated medication.

SUMMARY

In this disclosure, a convention is followed wherein the distal end of the device is the end closest to a patient and the proximal end of the device is the end away from the patient and closest to a practitioner.

A first aspect of the present invention pertains to a drug delivery device having a blunt needle component and a filter component. The blunt needle component includes an open distal end and a blunt needle extending from the open distal end to a first non-luer connector. The blunt needle of one or more embodiments has a length that is greater than 0.1 inches. In one or more specific embodiments, the blunt needle has a length that is greater than about 0.5 inches. The blunt needle also includes a lumen in fluid communication with the distal end of the blunt needle component. The blunt needle component of one or more embodiments includes a luer connector attached to the first non-luer connector and includes an open proximal end in fluid communication with the open distal end of the blunt needle.

The filter component of the drug delivery device includes an inlet for receiving the blunt needle, a second non-luer connector disposed adjacent to the inlet for engaging the first non-luer connector, an outlet and a filter attached to one or both of the inlet and the outlet in fluid communication with the inlet and the outlet. In one or more embodiments, the filter is disposed within a housing disposed between the inlet and the outlet. In one variant, the filter is disposed in a filter plate attached to one of the inlet and the outlet. The filter plate may include a first opening for attaching the filter plate to the outlet of the filter component and a second opening for attaching the filter plate to the inlet of the filter component.

The first non-luer connector of the blunt needle component and the second non-luer connector of the filter component are incompatible with standard luer connectors and intravenous route-accessing devices. In one or more specific embodiments, the second non-luer connector of the filter component is incompatible with standard syringe barrels.

In one variant, the first non-luer connector includes a collar that surrounds the blunt needle and includes an inside surface having threads disposed thereon for engaging an outwardly extending rib disposed on the second non-luer connector. In another variant, first non-luer connector includes an outside surface having threads disposed thereon for engaging corresponding threads disposed on an inside surface of the second non-luer connector. In one or embodiments, the cross-sectional widths of the inside and/or outside surfaces of the first non-luer connector and second non-luer connectors can be modified to be smaller than the cross-sectional width of standard luer connectors and intravenous route-accessing devices. Alternatively, the cross-sectional widths of the inside and/or outside surfaces of the first non-luer connector and second non-luer connectors can be modified to be larger than the cross-sectional width of standard luer connectors and intravenous route-accessing devices. The cross-sectional shape of the first non-luer connector and/or the second non-luer connectors may also be modified to prevent connection with standard luer connectors and intravenous route-accessingdevices. In one optional embodiment, one or both of the first non-luer connector and the second non-luer connector have non-circular cross-sectional shapes.

In one or more embodiments, the first non-luer connector and/or second non-luer connector may also incorporate connection mechanism selected from an interference fit, snap fit, locking means and combinations thereof. In one variant, the first non-luer connector and/or second non-luer connector may have structure that provides feedback upon engagement of the first non-luer connector with the second non-luer connector, which can include tactile feedback, audible feedback or both.

In one or more embodiments, the first non-luer connector and/or the second non-luer connector may be rotatable around the blunt needle. The blunt needle may also be rigid or non-rigid.

The luer connector of the blunt needle component may optionally include a permanent attachment element for forming a permanent attachment with an open tip of a syringe barrel. The luer connector may include a luer slip fitting or a luer lock fitting.

The outlet of the filter component may include a fitting for attaching the filter component to a catheter port. The fitting of the outlet may include a permanent attachment element for forming a permanent attachment with the cathether port. The outlet may also be rotatable.

A second aspect of the present invention pertains to a drug delivery device that includes a blunt needle component and a filter component with a valve that is configured to open upon application of a force distal direction by the blunt needle. In one or more embodiments, the blunt needle component includes an open distal end and extends from the open distal end to a first non-luer connector. The blunt needle may have a length of at least 0.5 inches and may also include a lumen in fluid communication with the open distal end. In one or more specific embodiments, the blunt needle may have a length in the range from about 0.5 inches to about 1.5 inches. The blunt needle component may also include a luer connector attached to the first non-luer connector and may include an open proximal end in fluid communication with the open distal end.

The filter component of embodiments according to the second aspect includes an inlet with an opening and a valve for receiving the blunt needle. A second non-luer connector is disposed adjacent to the inlet for engaging the first non-luer connector. The filter component also includes an outlet and a filter attached to one or both of the inlet and the outlet in fluid communication with the inlet and the outlet. The inlet of one or more embodiments may have a cross-sectional shape that is compatible with a cross-sectional shape of the blunt needle. In one variant, the inlet and the blunt needle have a non-circular cross-sectional shape.

In one or more embodiments, the valve may include a split septum and/or a check valve, which may be provided in the form of a ball valve or disc valve. The ball or disc valves may optionally be spring loaded. The valve may also be disposed within the inlet at a distance of at least 0.9 inches from the opening of the filter component.

A third aspect of the present invention pertains to a drug delivery device that includes a blunt needle component and a means for attaching the blunt needle to a filter component that includes an inlet and means for permitting and blocking fluid communication with the inlet. In one or more embodiments, the blunt needle component includes an open distal end, a blunt needle having a lumen in fluid communication with the open distal end. The blunt needle component may also include a luer connector attached to a first connector including an open proximal end in fluid communication with the open distal end. The drug delivery device includes an outlet and a filter attached to one or both of the inlet and the outlet in fluid communication with the inlet and the outlet.

In one embodiment, the means for permitting and blocking fluid communication comprises a second non-luer connector disposed on the filter component that prevents attachment of a luer connector, IV actuator mechanism and standard syringe barrel to the inlet. In such embodiments, the first connector may include a non-luer connector. In an alternative embodiment, the means for permitting and blocking fluid communication with the inlet includes a blunt needle having a non-luer cross-sectional shape that prevents attachment of a luer connector and IV actuator mechanism to the blunt needle component.

A fourth aspect of the present invention pertains to a method of delivering liquid medication to a catheter. In one or more embodiments, the method includes attaching a filter component to a catheter, wherein the filter component includes an inlet, an outlet and filter disposed between the inlet and the outlet. The method includes providing a blunt needle component and attaching the blunt needle to a tip of a syringe barrel. In one or more embodiments, the blunt needle includes an open distal end, a blunt needle having a lumen in fluid communication with the open distal end, a luer connector attached to a first non-luer connector including an open proximal end in fluid communication with the open distal end. In one or more embodiments, the method specifically includes attaching the tip of the syringe barrel to the open proximal end of the blunt needle component. The method also includes filling the syringe barrel with a pre-determined amount of liquid medication and attaching the blunt needle component to the filter component.

In one or more embodiments, the blunt needle has a length that extends into the inlet and a cross-sectional shape to form a fluid tight connection with the filter component. In another variant, the inlet of the filter component has a cross-sectional shape prevents fluid tight connection with a standard luer connector, IV actuator mechanism and standard syringe barrel.

A fifth aspect of the present invention pertains to a drug delivery device that includes a first adapter connector including a first non-luer fitting and a second adapter including a second non-luer fitting, wherein the first non-luer fitting and the second non-luer fitting are incompatible with standard luer fitting and intravenous route-accessing devices. In one or more embodiments, the first adapter includes a first open end including a first luer fitting, a second open end that includes the first non-luer fitting and a first main body having a hollow interior extending from the first open end to the second open end and in fluid communication with the first open end and the second open end. The second adapter of one or more embodiments includes a third open end including a second luer fitting and a fourth open end that includes the second non-luer fitting, a second main body having a hollow interior extending from the third open end to the fourth open end and in fluid communication with the third open end and the fourth open end.

In one or more embodiments, the drug delivery device includes a blunt needle component including an open distal end, a blunt needle extending from the open distal end to a first luer connection portion. The blunt needle has a length in the range of about 0.1 to about 1.5 inches and a lumen in fluid communication with the open distal end. The blunt needle component may also include a second luer connection portion attached to the first luer connection portion including an open proximal end in fluid communication with the open distal end, the first luer connection portion attached to the first luer fitting of the first adapter connector.

The drug delivery device according to the fifth aspect may also include a filter component including an inlet for receiving the blunt needle. The filter component may include a third luer connection portion disposed adjacent to the inlet and attached to the second luer fitting of the second adapter connector. The filter component may also include an outlet and a filter attached to one or both of the inlet and the outlet in fluid communication with the inlet and the outlet.

In one or more embodiments, the first main body of the first adapter connector comprises a valve for receiving the blunt needle and configured to open upon application of a force in the distal direction by the blunt needle. The valve may include a split septum or a check valve.

BRIEF DESCRIPTION OF THE DRAWINGS

FIG. 8 shows a perspective view of a blunt needle component according to one or more alternative embodiments of the present invention;

FIG. 9 illustrates a cross-sectional view of the blunt needle component shown in FIG. 8 taken along line 9-9;

FIG. 11 shows a perspective view of a blunt needle component according to one or more alternative embodiments of the present invention;

FIG. 12 illustrates a cross-sectional view of the blunt needle component shown in FIG. 11 taken along line 12-12;

FIG. 25 illustrates a cross-sectional view of the filter component of FIG. 24 taken along line 25-25;

FIG. 26 shows a perspective view of the filter component of FIG. 24 assembled with a blunt needle component and a syringe barrel;

FIG. 30 illustrates a first piece and a second piece of a pair of adaption connectors; and FIG. 31 illustrates an exploded cross-sectional view of the first piece and the second piece shown in FIG. 30, taken along line 31-31.

DETAILED DESCRIPTION

Figure 1:
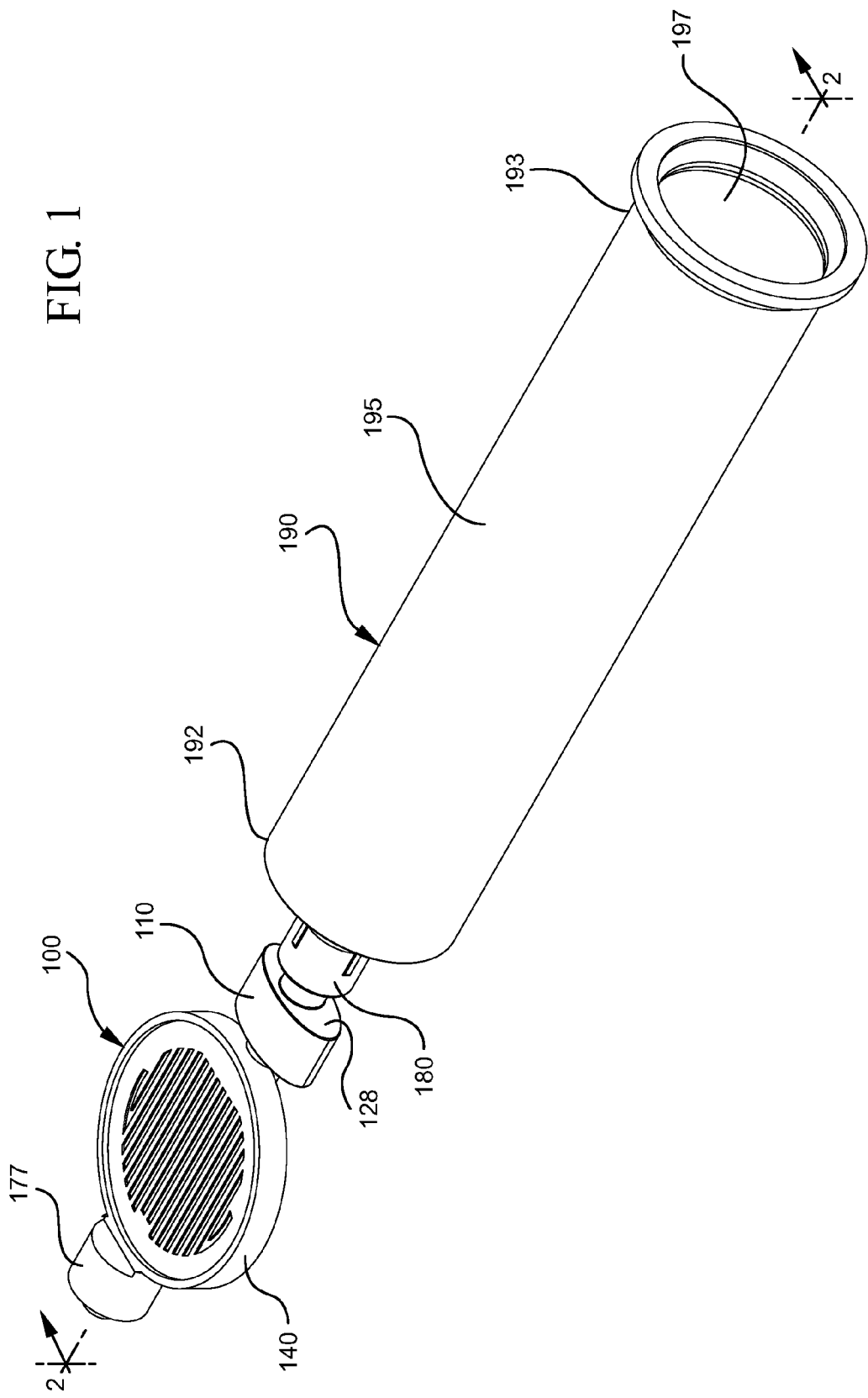
FIG. 1 illustrates a perspective view of a blunt needle component and a filter component attached to a syringe barrel, according to one or more embodiments of the present invention.

Before describing several exemplary embodiments of the invention, it is to be understood that the invention is not limited to the details of construction or process steps set forth in the following description. The invention is capable of other embodiments and of being practiced or being carried out in various ways.

A first aspect of the invention pertains to a drug delivery device including a blunt needle component 110 with a first non-luer connector 120 and a filter component 140 with a second non-luer connector 160, wherein the first non-luer connector 120 and the second non-luer connector 160 reduce misconnection of the drug delivery device to incorrect route-accessing devices. The second aspect of the present invention pertains to a drug delivery device 400 including a blunt needle component 410 and a filter component 440, wherein a second non-luer connector 460 of the filter component 440 extends proximally from a filter housing 450. A third aspect of the present invention pertains to an adapter 600 for use with a drug delivery device 500, which utilize a luer connector. A fourth aspect of the present invention pertains to adaption connectors 900 which attach to luer connectors on existing drug delivery devices and provide non luer connectors to the drug delivery devices that reduce misconnection.

FIGS. 1-13 illustrate a drug delivery device 100 including a blunt needle component 110 and a filter component 140, according to a first aspect of the present invention. FIG. 1 shows the filter component 140 assembled with the blunt needle component 110 and attached to a syringe barrel 190. The blunt needle component 110 includes a first non-luer connector 120 and the filter component 140 includes a second connector non-luer 160. The first non-luer connector 120 and the second non-luer connector 160 are shaped and adapted to engage to form a fluid tight connection between the blunt needle component 110 and the filter component 140.

FIGS. 6-9 and 11-12 illustrate embodiments of a blunt needle component 110 according to one or more embodiments of the present invention. The blunt needle component 110 comprises an open distal end 111, an open proximal end 119. The blunt needle component 110 also includes a blunt needle 112 extending from the open distal end 111 to the first non-luer connector 120. The blunt needle 112 has an elongate shape and includes a distal open end 114 and a proximal open end 116 attached to the first non-luer connector 120. The blunt needle 112 has a sidewall 118 extending from the proximal open end 116 to the distal open end 114. The sidewall 118 may have an elongate tubular shape or other elongate shape that includes a lumen 117 in the center. The blunt needle 112 may optionally have pores (not shown) through the side wall 118.

The blunt needle 112 has a length sufficient permit fluid-tight engagement between the first non-luer connector 120 and the second connector 160, as will be disclosed below. In one or more embodiments, blunt needle 112 has a length that is sufficient to extract a liquid from a glass ampoule or vial. The blunt needle 112 may also have a length that is longer than a standard tip of a syringe barrel and/or permits the blunt needle 112 to open valves disposed on containers and/or reach the bottom of a vial or other container. In other words, the blunt needle 112 has a length that permits the blunt needle component to be used to draw up liquid from a vial or ampoule into the syringe barrel 190 and then administer or deliver the liquid to the filter component 140 without having to attach a separate needle hub or other adapter. Moreover, the length of the blunt needle 112 must be sufficient to permit fluid-tight engagement between the first non-luer connector 120 and the second connector 160, upon attachment to the filter component 140.

In one or more embodiments, the blunt needle 112 may have a length that is greater than about 0.1 inches. The blunt needle 112 of one or more embodiments has a length that is greater than about 0.5 inches. The length of the blunt needle 112 may also be greater than 0.55 inches, 0.6 inches, 0.75 inches, 1.0 inches, 1.25 inches, 1.5 inches, 1.75 inches, 2.0 inches, 2.25 inches or 2.5 inches. In one variant, the blunt needle 112 has a length in the range from about 0.1 to about 2.5 inches. In another variant, the blunt needle 112 may have a length in the range from about 0.5 to about 2.5 inches. In yet another variant, the blunt needle 112 may have a length in the range from about 0.5 inches to about 1.5 inches. In a specific embodiment, the blunt needle 112 may a length in the range from about 0.5 inches to about 1.25 inches. In an even more specific embodiment, the blunt needle 112 may have a length in the range from about 0.5 to about 1.0 inches. In one or more embodiments, the blunt needle has a length of about 1.0 inch. The blunt needle 112 may be made from plastic material or metal. Examples of suitable plastic material include polypropylene, polycarbonate and combinations thereof. Examples of suitable metals include stainless steel.

In one or more embodiments, the blunt needle 112 may include an inside surface 113 and an outside surface 115 that has a uniform cross-sectional width or diameter. In one variant, the blunt needle 112 may have a cross-sectional width or diameter in the range from about 0.05 inches to about 0.15 inches. In one or more alternative embodiments, the outside surface 115 may include a cross-sectional width that permits fluid tight connection within the second connector 160, which will be described in more detail below.

The blunt needle 112 and the blunt needle component 110 may be used to withdraw a drug from a glass ampoule and can be used to access an epidural filter or catheter connector through the inlet of the filter component 140, which will be described below. The blunt needle 112 also prevents needle stick during use. In addition, the as the blunt needle 112 can be used to aspirate and administer a drug to a catheter connector, there are fewer connection steps. For example, in conventional drug delivery systems which incorporate a filter component, a needle cannula is attached to the syringe barrel so that a liquid can be aspirated into the syringe barrel. The needle cannula must typically be removed before the aspirated liquid can be administered to a filter component. In the embodiments disclosed herein, the blunt needle 112 of the blunt needle component 110 can be used for both aspirating the liquid into the syringe barrel and for administering the aspirated liquid into the filter component. The use of a single component for aspiration and administration of liquid also provides ease of use and reduces manufacturing costs. In addition, the use of a single component for aspiration and administration of a drug also causes less confusion and requires less education often due to the introduction of a new product.

Figure 2:
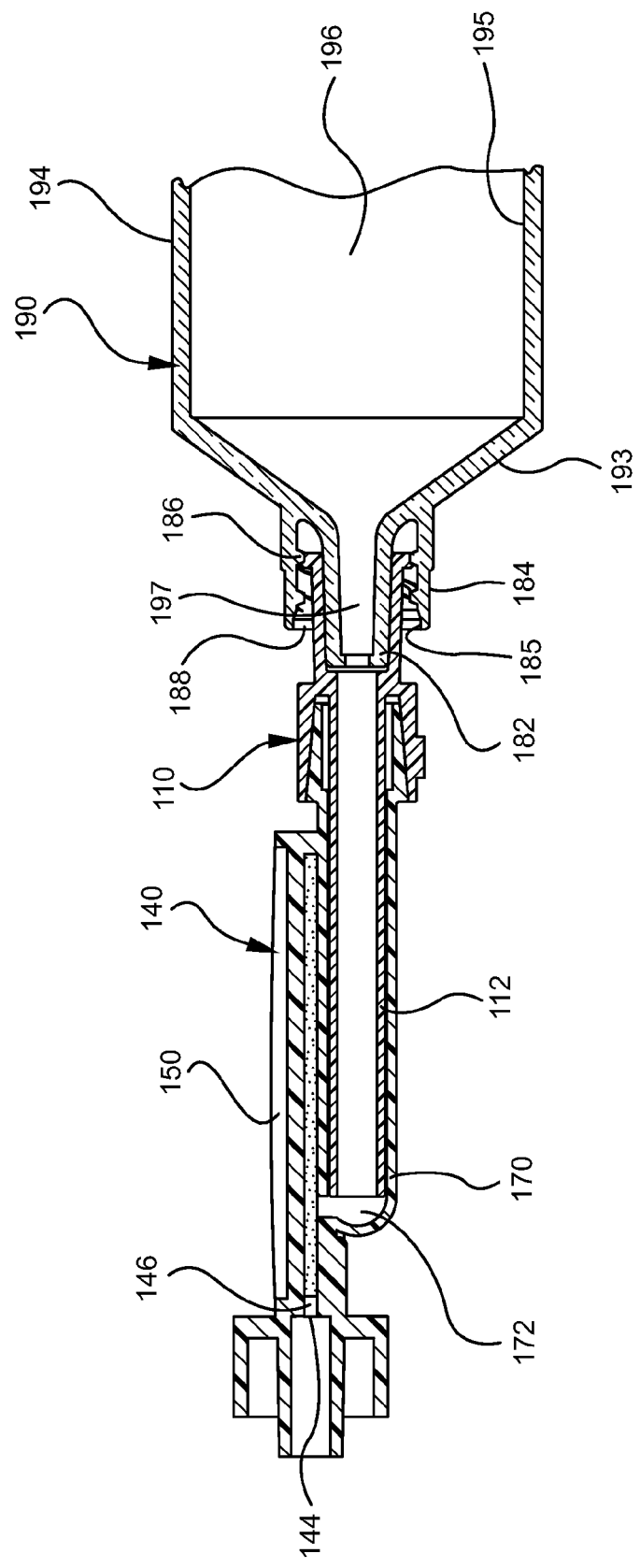
FIG. 2 illustrates a partial cross-sectional view of the blunt needle component, filter component and syringe barrel shown in FIG. 1 taken along line 2-2.
Figure 3:
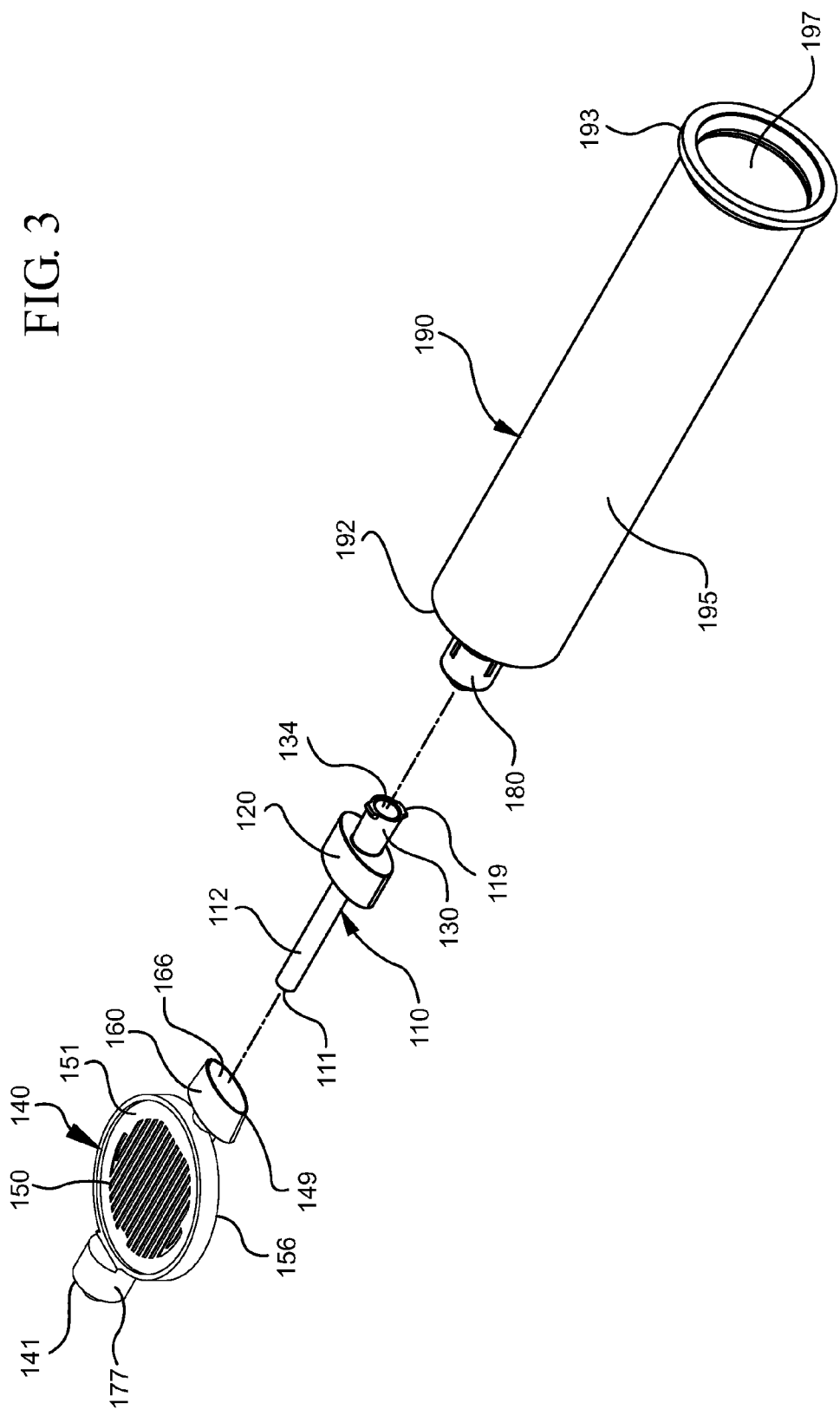
FIG. 3 illustrates an exploded view the blunt needle component, filter component and syringe barrel shown in FIG. 1.

In one or more alternative embodiments, the blunt needle component 110 is free of a non-luer portion 120 (not shown). In such embodiments, the blunt needle 112 has a shape or dimension that allows the blunt needle 112 to function as a no-luer connector for attachment of the blunt needle component 110 to the filter component 140 and, specifically the second connector 160. An example of these embodiments will be discussed below in more detail. A luer portion in the form of a hub connector 130 is attached to the first non-luer portion 120 and allows attachment of the blunt needle component 110 to standard syringe barrels that include a luer fitting, without the need for additional adapters or other means for enabling the attachment. The hub connector 130 shown in FIGS. 1-13 form part of the proximal open end 116 of the blunt needle 112. The hub connector 130 is shaped to be connected or attached to a fluid source or container, for example a syringe barrel, as shown in FIGS. 1-3. The hub connector 130 shown in FIGS. 6-7 includes a standard luer connector for attachment to a luer lock or luer slip fitting on the fluid source or container. As is understood in the art, a luer lock fitting includes a male conical fitting in a coaxial relationship with an internally threaded collar. A luer slip fitting includes a male conical fitting with no internally threaded collar. The hub connector of the blunt needle components described herein eliminates the need to re-design or alter existing syringe barrels or other fluid containers that utilize a luer fitting.

Figure 6:
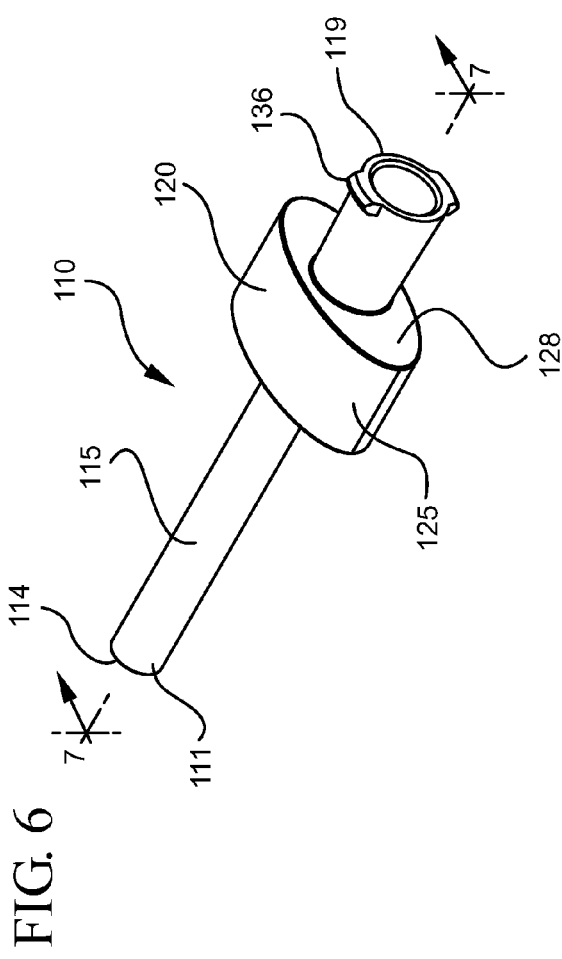
FIG. 6 illustrates a perspective view of the blunt needle component shown in FIG. 1.
Figure 7:
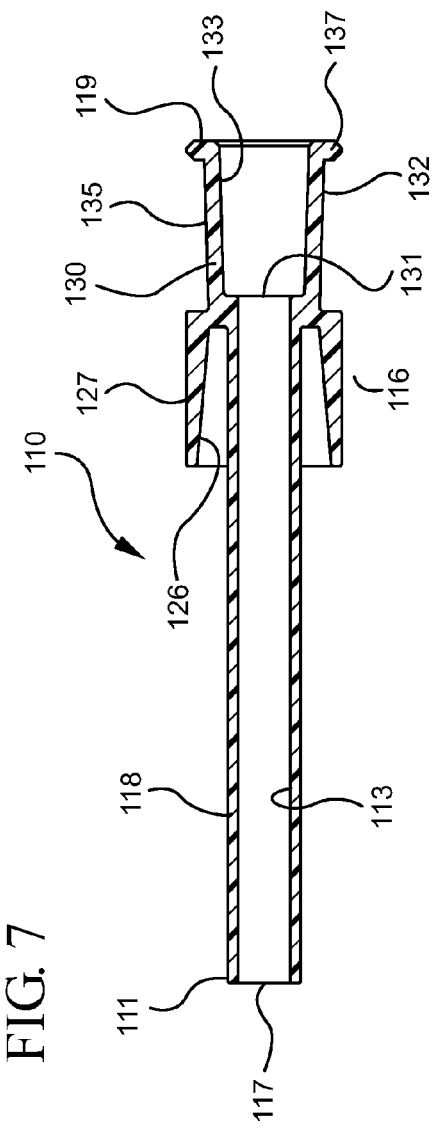
FIG. 7 shows a cross-sectional of the blunt needle component illustrated in FIG. 6 view taken along line 7-7.

The hub connector 130 shown in FIGS. 6-7 includes an open distal end 131 disposed adjacent to the first non-luer connector 120 of the blunt needle component 110 and a sidewall 132 extending from the first non-luer connector 120 to the open proximal end 119 of the blunt needle connector 110. The sidewall 132 includes an inside surface 133 defining a hub cavity 134 for receiving a luer lock or luer slip fitting. The inside surface 133 of the sidewall 132 is tapered to have a cross-sectional width that increases from the first non-luer connector 120 to the proximal end 119. The tapered shape of the sidewall 132 allows the inside surface 133 of the hub connector to engage the male conical fitting of a luer slip fitting. The hub connector 130 includes an outside surface 135 and a radially outwardly extending portion 136 disposed on the outside surface 135 that engages a threaded internal collar of a luer lock fitting. The radially outwardly extending portion 136 may include at a pair of ribs 137, as shown in FIGS. 6-9 and 11-12. In one or more embodiments, the radially outwardly extending portion 136 may include a single rib (not shown), or, in one or more specific embodiments, the radially outwardly extending portion 136 may include a peripheral lip (not shown) that is disposed on the outside surface 135 along the circumference of the hub connector 130. For illustration, the hub connector 130 is shown in FIGS. 1-3 attached to a syringe barrel 190. Other fluid containers may be utilized which include a standard luer fitting, including either a luer lock fitting or a luer slip fitting, as will be described in more detail below.

In one or more embodiments, permanent connection mechanisms may be built in the hub connector 130, so that, upon connection of blunt needle component 110 to syringe barrel 190 or other container, the connection becomes permanent and the blunt needle component 110 and syringe barrel 190 or other container are not detachable. The permanent connection can be realized by welding, which may include ultrasonic welding, gluing, or through design, for example, by incorporating one or more ratchet connector, special threads and other structures known in the art.

The first non-luer connector 120 is disposed at the proximal open end 116 of the blunt needle 112 and is attached to the hub connector 130. The first non-luer connector 120 includes a distally extending wall 125 that is coaxially disposed around the blunt needle 112 and extends toward the open distal end 111 of the blunt needle component 110. The distally extending wall 125 defines an annular space 124 between the distally extending wall 125 and the blunt needle 112. In one or more embodiments, the annular space 124 is configured or shaped to receive the second non-luer connector 160. In one or more alternative embodiments, the distally extending wall 125 is shaped or configured to engage the second non-luer connector 160. In one or more embodiments, the distally extending wall 125 is rotatable around the blunt needle 112 to facilitate connection between the blunt needle component 110 and the filter component 140, without rotating the syringe barrel 190. The first non-luer connector 120, including the distally extending wall 125 and/or the annular space 124, of the first non-luer connector 120 is shaped to prevent attachment of the blunt needle component 110 to an unintended or incompatible filter component or other device. Examples of such devices include standard IV route-accessing devices, including, without limitation, blunt cannula split-septum, luer access mechanical valves, luer access mechanical valves with positive displacement, luer access split-septa. Specifically, fluid-tight engagement of the first non-luer connector 120 to any device requires a compatible opening. As will be discussed below, the second non-luer connector 160 of the filter component 140 includes such a compatible opening.

In the embodiments shown in FIGS. 1-13, the distally extending wall 125 includes an inside surface 126 which is shaped to form a fluid-tight engagement with the outside surface of the second non-luer connector 160. In one or more embodiments, the inside surface 126 of the first non-luer connector 120 and the outside surface of the second non-luer connector 160 may be correspondingly tapered to form a friction fit engagement. The first non-luer connector 120 may include an outside surface 127 which may be tapered to form a frictional engagement with the inside surface of the second non-luer connector 160. In one or more alternative embodiments, the inside surface 126 of the first non-luer connector 120 may include a threaded surface (not shown), which engage a corresponding structure (not shown) disposed on the outside surface of the second non-luer connector 160. Alternatively, the threaded surface (not shown) may be disposed on the outside surface of the second non-luer connector 160 to engage with a corresponding structure (not shown) disposed on the inside surface 126 of the first non-luer connector 120.

Figure 4:
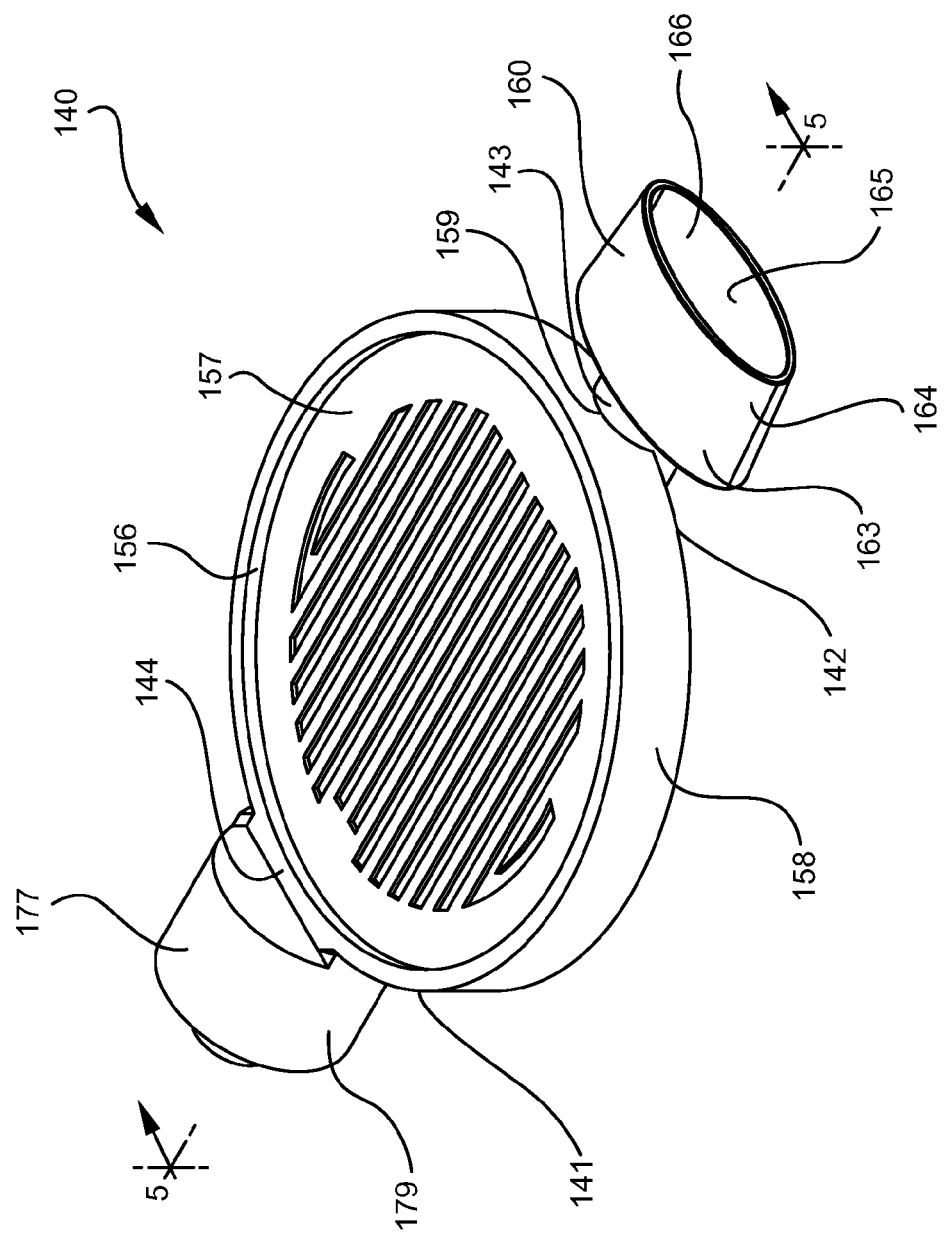
FIG. 4 illustrates a perspective view of the filter component shown in FIG. 1.
Figure 5:
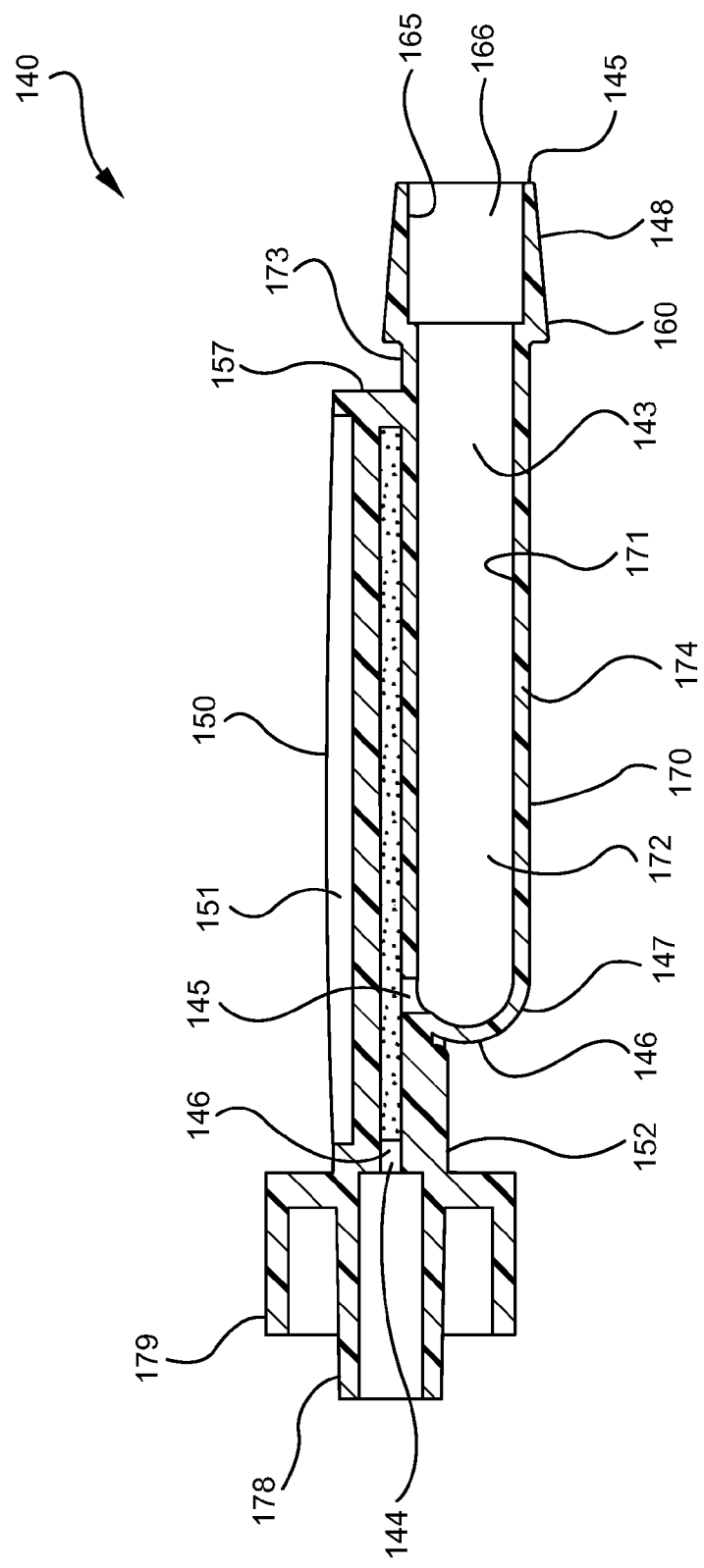
FIG. 5 shows a cross-sectional view of the filter component illustrated in FIG. 4 taken along line 5-5.

The filter component 140, as more clearly shown in FIGS. 4-5, includes a distal end 141, a proximal end 142 and a filter housing 150 extending from the distal end 141 to the proximal end 142. The filter component 140 also includes an inlet 143 disposed at the proximal end 142 and an outlet 144 disposed at the distal end 141.

The inlet 143 includes an opening 145 to a filter cavity 146 enclosed within the filter housing 150 so the inlet 143 and the filter cavity 146 are in fluid communication. The inlet 143 includes a distal end 147 and a proximal end 148 and may be shaped to receive the blunt needle 112 of the blunt needle component 110. The inlet 143 shown in FIGS. 1-13 includes a partially enclosed tubular body 170 extending from the opening 145 and having an inside surface 171 defining a channel 172 that has an elongate shape to receive the blunt needle 112. The partially enclosed tubular body 170 includes a first portion 173 extending from the distal end 147 of the inlet 143 to a second portion 174, wherein the first portion 173 is completely enclosed. The second portion 174 extends from the first portion 173 to the proximal end 142 of the inlet 143 and includes a notched opening 175 allowing fluid communication between the opening 145 of the inlet 143 and the filter cavity 146. The distal end 141 of the inlet 143 includes a closed end 146 that has a curved shape. In one or more alternative embodiments, the closed end 176 may be shaped to have a linear end or an end that has that is perpendicularly disposed with regard to the partially enclosed tubular body 170.

In the embodiment shown in FIGS. 1-13, the inlet 143, including the partially enclosed tubular body 170, is disposed adjacent to the filter housing 150. The orientation of the inlet 143 is parallel to the filter housing 150 and notched opening 175 of the inlet extends into the filter housing 150. The notched opening 175, shown in FIGS. 4-5, is disposed at a point within the filter housing 150 at a distance from the opening 145. In one or more embodiments, the inlet 143 may be disposed at an angle between 0 degrees to 90 degrees from the filter housing 150 to facilitate connection and injection when the filter component 140 is taped or otherwise attached to a patient body.

The inside surface 171 of the tubular body 170 may have a cross-sectional width or diameter that permits formation of a fluid tight seal with the outside surface 115 of the blunt needle 112. In one or more embodiments, the inside surface 171 may have a varying cross-sectional width or diameter that corresponds to a varying cross-sectional width or diameter of the outside surface 115 of the blunt needle 112 to enable formation of a fluid tight seal with the blunt needle 112 component and to prevent such formation with other devices.

The filter component 140 includes a filter 149 or filter membrane disposed within the filter housing 150. The filter 149 may include filtration material known in the art, which may include particles, fibers and combinations thereof. In one variant, the filter material may include polyethersulfone. The filter 149 is disposed in the fluid path of the filter component 140. In one or more specific embodiments, the filter 149 may be attached to one or both of the inlet 143 and the outlet 144 such that the filter 149 is in fluid communication with the inlet 143 and the outlet 144. In such embodiments, the fluid entering the inlet 143 and exiting through the outlet 144 passes through the filter 149. The filter 149 may also be disposed within the filter cavity 146 of the filter housing. In a specific embodiment, the cavity 154 may include a plurality of barriers for supporting and dispersing the filter within the cavity. In one or more embodiments, the cavity may contain both the plurality of barriers and filter materials.

In one or more embodiments, the filter 149 may be disposed within the inlet 143 or, specifically, within the channel 172 of the partially enclosed tubular body 170 of the inlet. In one or more alternative embodiments, the filter housing 150 may include a filter plate that is attached to the inlet 143. Other means and structures for attaching the filter housing to the inlet 143 may also be utilized.

The second non-luer connector 160 is disposed adjacent to the inlet 143 for attaching the filter component 140 to the first non-luer connector 120 of the blunt needle component 110. The second non-luer connector 160 includes a proximally extending wall 164 that extends in the proximal direction from the inlet 143 and includes an inside surface 165 that defines an inlet chamber 166. In one or more embodiments, the inlet chamber 166 receives a portion of the blunt needle component 110 to secure attachment of the filter component 140 thereto. In the embodiment shown, the inlet chamber 166 may receive the first non-luer connector 120 of the blunt needle component 110. In one or more alternative embodiments, the proximally extending wall 164 may include an outside surface 163 for engaging the inside surface 126 of the first non-luer connector 120. The proximally extending wall 164 may be optionally rotatable such that it rotates around the blunt needle 112 during attachment to facilitate the connection between the first non-luer connector 120 and the second non-luer connector 160 without rotating the filter component 140. Such rotation of the proximally extending wall 164 would also prevent catheter kinking. The proximally extending wall 164 of the second non-luer connector 160 is shaped to prevent attachment of the filter component 140 to an unintended or incompatible fluid source or container. For example, the wall second non-luer connector 160 is incompatible and cannot be connected to standard syringe that includes a standard luer fitting. In the embodiments shown in FIGS. 1-13, the second non luer connector 160 of the filter component 140 is shaped to engage the first non-luer connector 120.

The filter housing 150 shown in FIGS. 1-13 has a disc-shaped configuration, however, the filter housing 150 may be shaped to be cylindrical or have any other shape. The filter housing 150 may include two plates 151, 152 that are joined together. The plates may be formed from a polymer material such as polycarbonate to form the filter cavity 146. In a specific embodiment, the plates 151, 152 are welded together, for example, using ultrasonic welding techniques known in the art, and/or glued together, using methods known in the art. In the embodiment shown in FIGS. 1-5, the plates 151, 152 are identical and include a peripheral edge 156. The plates 151, 152 may be concavely shaped or may be flat. In one or more embodiments, one or both of the plates 151, 152 may have different shapes and/or sizes. In the embodiment shown in FIG. 1, each of plates 151, 152 may also include an edge wall 158 extending from the peripheral edge 156 at an angle of about 90 degrees with respect to the plates 151, 152. In the embodiment shown, the edge wall 158 extends perpendicularly beyond the plates 151, 152. In one or more embodiments, the edge wall 158 extends perpendicularly and outwardly from the peripheral edge 156 of the plates 151, 152. In a specific embodiment, the angle of the edge wall 158 with respect to each plate is in the range from about 45 degrees to 180 degrees. In a more specific embodiment, the angle of the edge wall 158 with respect to the plate is in the range from about 45 degrees to about 135 degrees. To form the housing, the edge walls 158 of the plates 151, 152 are joined to form the filter cavity 146 having a disc shape.

In a specific embodiment, one of the plates 151, 152 may include an edge wall 158 while the second of the plates 151, 152 is free of an edge wall 158. In such embodiments, to form the housing 150, the edge wall 158 of one of the plates 151, 152 is joined to the peripheral edge 156 of the other of plates 151, 152. In a more specific embodiment, both plates 151, 152 are free of an edge wall 158 and a separate edge wall 158 component having a first rim (not shown) and second rim (not shown) is used to join the plates 151, 152. In such embodiments, the first rim (not shown) is welded to the peripheral edge 156 of one of the plates 151, 152 and the second rim (not shown) of the edge wall 158 is welded to the peripheral edge 156 of the other of plates 151, 152.

In one or more embodiments, the first portion 173 of the inlet 143 is attached to the edge wall 158 of the filter housing 150. A link portion 157 may bridge or connect the first portion 173 to the edge wall 158 of the filter housing 150. In the embodiment shown, the edge wall 158 includes a cutout portion 159 to accommodate the first portion 173. In one or more alternative embodiments, one of the plates 151, 152, may include an indented portion (not shown) to accommodate the partially enclosed tubular body 170. In one or more embodiments, one of the plates 151, 152 includes an aperture (not shown) and the notched opening partially enclosed tubular body 170 is attached to the aperture (not shown) such that the notched opening 175 of the partially enclosed tubular body 170 is in fluid communication with the filter cavity 146 of the filter housing 150.

In one or more alternative embodiments, the filter housing may have a cylindrical shape (not shown) and include a hollow cylindrical body (not shown). The hollow cylindrical body (not shown) may include a groove (not shown) and an orifice (not shown) for attachment of the partially enclosed tubular body 170 to the filter housing 150.

The outlet 144 of the filter component 140 may be disposed at the opposite end of the filter component 140 from the inlet 143. In one or more embodiments, the outlet may be located in one of the plates 151, 152 (not shown) or may be disposed adjacent to the inlet 143 (not shown). As shown in FIG. 5, the outlet 144 includes a luer lock fitting 177 comprising a male conical fitting 178 in a co-axial relationship with an internally threaded collar 179. In one or more alternative embodiments, the outlet 144 may include a luer slip fitting (not shown) including a male conical fitting without a collar (not shown). In one or more specific embodiments, the outlet may include a non-luer fitting, as described herein. The luer lock fitting 177 of FIGS. 1-13 can be readily mated with a catheter connector or catheter port having a corresponding and compatible luer structure. In one or more embodiments, the luer lock fitting 177 is rotatable to facilitate connection between the catheter (not shown) and the outlet 144 without rotating the filter component 140 and/or the catheter (not shown). Such rotation of the luer lock fitting 177 would prevent catheter kinking.

In one or more embodiments, the outlet 144 may be pre-assembled to the catheter connector and/or may also be removable from such connection. Permanent connection mechanisms may also be built in the outlet 144 so that, upon connection of outlet 144 to a catheter connector (not shown) or other drug delivery site, the connection becomes permanent and the filter component 140 and the catheter connector (not shown) are not detachable. The purpose of the permanent connection is to prevent disconnections between the filter component 140 and catheter connectors or other drug delivery sites, leaving only the joint between the filter component 140 and the blunt needle component 110 being detachable. The permanent connection can be realized by welding, which may include ultrasonic welding, gluing, or through design, for example, by incorporating one or more ratchet connector, special threads and other structures known in the art. In one or more embodiments, the filter component 140 may be integrally formed or integrated with the catheter connector.

In the embodiment shown in FIGS. 6-7, the first non-luer connector 120 of the filter component 140 includes a distally extending wall 125 having an oval cross-section and a connecting section 128 between the distally extending wall 125 and the hub connector 130. The oval cross-section of the distally extending wall 125 is incompatible or prevents the attachment of luer connectors, which have circular openings, are conically shaped conical and/or meet the definition of ISO 594 parts 1 and 2. In the embodiment shown in FIGS. 1-5, the second non-luer connector 160 has a corresponding oval cross-section, which is incompatible or prevents the attachment of luer connectors, which have circular openings, are conically shaped conical and/or meet the definition of ISO 594 parts 1 and 2, but is compatible with the first non-luer connector 120. Other examples of first non-luer connectors are shown in FIGS. 6-9 and 11-12.

An alternative embodiment of a blunt needle component 210 having a distal end 211, a proximal end 219 and a first non-luer connector 220 is shown in FIGS. 6-7. The first non-luer connector 220 has a square cross-section and includes a 224 bridge portion connecting the first non-luer connector 220 to a blunt needle component. The first non-luer connector 220 includes four walls 221, 222, 223, 224 each having two side edges 225 each, wherein all four walls are joined by at least two side edges 225 to each other to form a hollow square configuration having four sides that surround a blunt needle 212 in which the bridge portion 224 forms part of a fifth side. A hub connector 230 extends from the first non-luer component 220 to the proximal end 219 of the blunt needle component. The hub connector 230 shown includes a luer fitting capable of connecting to luer slip or luer lock fittings. The filter component 240 shown in FIG. 10 includes a second non-luer connector 260 having a corresponding square cross-section with a corresponding linking portion 267. The second non-luer connector 260 includes four walls 261, 262, 263, 264 each having a side edge 265, wherein all four walls are joined at least two side edges 265 to each other to form a hollow square configuration having four sides that form a inlet cavity 266 having a square cross-section, in which the linking portion 267 forms part of a fifth side.

Figure 13:
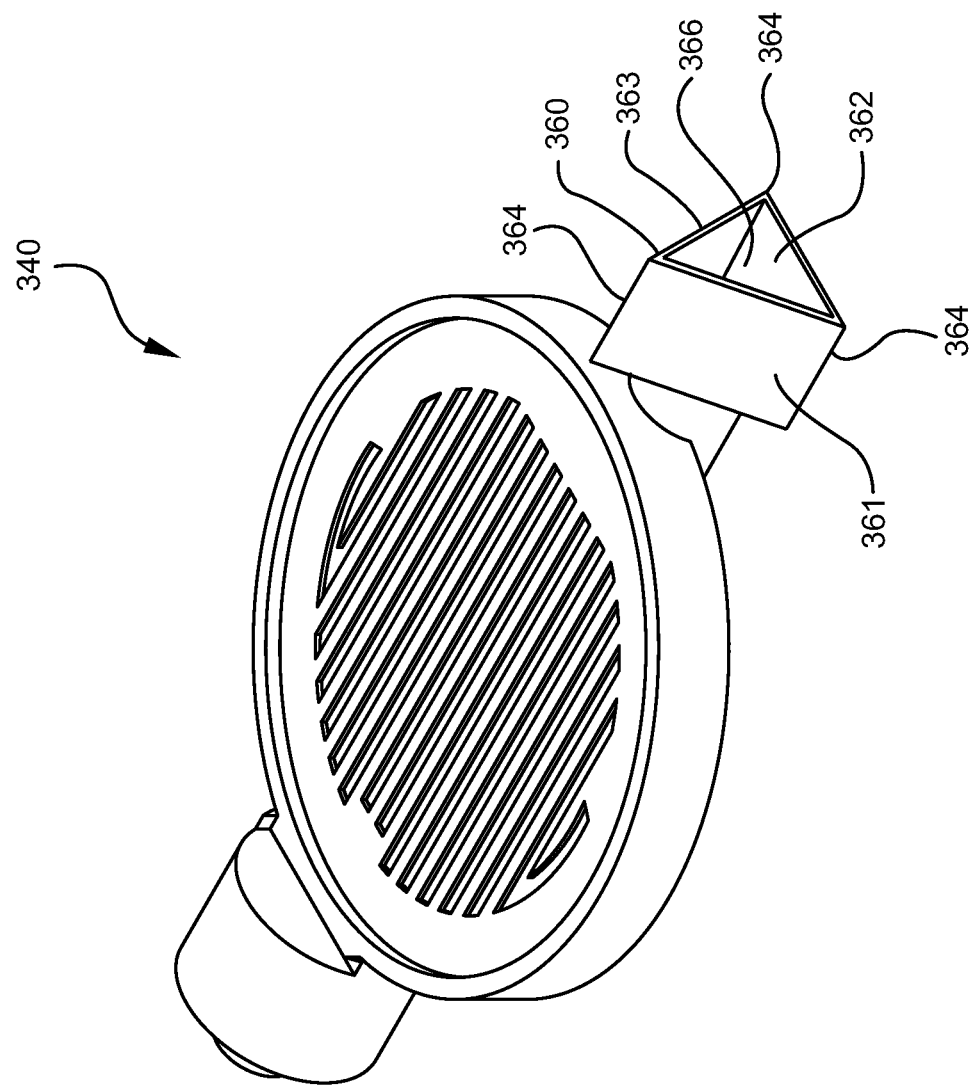
FIG. 13 illustrates a perspective view of a filter component according to one or more embodiments.

FIGS. 11-12 shows another embodiment of a blunt needle component 310 having a distal end 311, a proximal end 319 with a first non-luer connector 320 having a triangular cross-section. The first non-luer connector 320 includes three walls 321, 322, 323 each having two side edges 324 each, wherein all three walls are joined by at least two side edges 225 to each other to form a hollow triangular configuration having three ides that surround a blunt needle 312 in which the bridge section 325 forms part of a fourth side. A hub connector 330 extends from the first non-luer component 320 to the proximal end 319 of the blunt needle component. The hub connector 330 shown includes a luer fitting capable of connecting to luer slip or luer lock fittings. FIG. 13 illustrates a filter component 340 with a second non-luer connector 360 having a triangular cross-section. The second non-luer connector 360 includes three walls 361, 362, 363, each having two side edges 364 each, wherein all three walls are joined at least two side edges 264 to each other to form a hollow triangular configuration having three sides that form a inlet cavity 366 having a triangular cross-section, in which the linking section (not shown) forms part of a fourth side.

In one or more embodiments, the first non-luer connector may have a tab that extends inwardly and the second non-luer connector may include an opening for engaging the tab, for fluid tight engagement of the first and second non-luer connectors. Other configurations may include a having a first non-luer connector and/or second non-luer connector with larger or smaller cross-sectional widths than standard luer connectors. In one or more embodiments, the engagement between the first non-luer connector and/or the second non-luer connector may include a threaded portion (not shown), wherein the direction of the threaded portion may be reversed from clockwise to counterclockwise. In one or more alternative embodiments, the first non-luer connector and the second non-luer connector may have reversed male and female connections. For example, the internal threaded portion may be disposed on one of the first and second connection having a female fitting with the external threads or a tab capable of engaging the internal threads on the female fitting disposed on the outside surface of the other of the first and second connection having a male fitting.

One or more alternative embodiments may incorporate different connecting mechanisms to join the first and second non-luer connectors described herein. For example, the inside and/or outside surfaces of one of the first and second non-luer connectors may be shaped to form an interference fit connection with only the corresponding inside or outside surface of the other of the first and second non-luer connectors. Alternatively, the first and second non-luer connectors may include structure to enable a snap fit connection or may include a locking or latching mechanism. One or more embodiments may incorporate a connection that features an audible or tactile feedback indicating proper connection between the first and second non-luer connectors.

One or more embodiments of the present invention according to the first aspect may include other means for preventing incorrect connections to the blunt needle component 110 and/or the filter component 140. In one or more embodiments, the inlet 143 of the filter component 140 may include a valve (not shown). The valve may be a one-way or check valve that requires application of a force on the valve in the distal direction to open the valve and to permit access to the filter component. Specifically, such a valve may include a ball valve, a flap valve, or other known one-way valves known in the art. The valve may be spring-loaded (not shown). To gain access to the filter component 140 and the catheter connector (not shown), the blunt needle 112 would need to be inserted into the inlet 143 and exert a force on the valve in the distal direction to open the valve. The opening of the valve would permit the blunt needle component 110 to form a fluid tight engagement and allow fluid communication between the syringe or other fluid container attached to the blunt needle component 110 and the filter component 140. In such embodiments, the valve (not shown) would be disposed within the channel 172 of the partially enclosed tubular body 170 so that it could only be opened by a blunt needle 112, as described herein, having a sufficient length. In such embodiments, standard luer slip tips, which typically are 0.4 inches in length, would not have sufficient length to be able to open the valve.

In one or more alternative embodiments, the valve may include a split septum (not shown). The split septum may be attached to the proximal end 148 of the inlet. The split septum may be swabable and provides a barrier to microbials and other contaminants. To gain access to the filter component 140 and the catheter connector (not shown), the blunt needle 112 would need to be inserted into the inlet 143 and exert a force on the split septum in the distal direction to open the split septum. The opening of the split septum would permit the blunt needle component 110 to form a fluid tight engagement and allow fluid communication between the syringe or other fluid container attached to the blunt needle component 110 and the filter component 140.

Means for preventing reuse of a blunt needle to access IV routes may also be incorporated. For example, the blunt needle 112 may be non-rigid. In such embodiments, the entire blunt needle 112 or a portion of the blunt needle 112, for example, the portion adjacent to the distal open end 114, may be made from a soft plastic material such that when the blunt needle 112 is used to activate the valve or separate the split septum of other devices, the blunt needle will bend and would be prevented from accessing the IV route. In one or more embodiments, the entire blunt needle 112 or a portion of the blunt needle 112, for example, the portion adjacent to the distal open end 114, may have a small outside diameter and/or may include a thin wall such that when the blunt needle 112 is used to activate the valve or separate the split septum of other devices, the blunt needle will bend and would be prevented from accessing the IV route. In one or more alternative embodiments, the entire blunt needle 112 or a portion of the blunt needle 112, for example, the portion adjacent to the distal open end 114 may have a large outside diameter such that the blunt needle 112 is not able to fit in or form fluid tight engagement in IV route-accessing devices.

In one or more alternative embodiments, color codes, labels, engraved labels and the like may be incorporated into the blunt needle component 110 and/or the filter component 140 to reduce misconnection. For example, the blunt needle component 110 and the filter component 140 may include labels which state "for epidural only" to indicate to a practitioner that the blunt needle component 110 and the filter component 140 are for epidural use and should not be used with IV route-accessing devices.

To assemble the drug delivery device 100 and to administer a drug to a catheter connector (not shown), the blunt needle component 110 is disposed between the filter component 140 and the syringe barrel 190 (or other fluid container), as shown in FIG. 3. The outlet 144 of the filter component 140 may be attached to a cathether connector (not shown) so the inlet 143 of the filter component 140 is ready to receive the blunt needle component 110. In one or more embodiments, before attaching the blunt needle component 110 to the filter component 140, the syringe barrel 190 or other fluid container is filled with a predetermined amount of a drug to be administered through the filter component 140 and catheter connector (not shown). The syringe barrel 190 may be provided empty, however, in one or more alternative embodiments, the syringe barrel may be provided pre-filled.

In one or more embodiments, the drug is aspirated into the syringe barrel 190 by attaching the hub connector 130 of the blunt needle component 110 to a syringe barrel or other fluid container. For illustration, FIGS. 1-3 show a syringe barrel 190 that includes a distal end 191 and an open proximal end 192 and an end wall 193. A sidewall 194 may extend from the distal end 191 to the open proximal end 192 and may include an interior surface 195 that defines a chamber 196 for holding liquids. The distal end 191 of the syringe barrel 190 may also include an opening 197 in fluid communication with the chamber 196. In the embodiment shown in FIGS. 1-3, the distal end 191 of the syringe barrel includes a luer lock fitting 180 including an elongate tip 182 forming a male fitting surrounding the opening 197 and a collar 184 coaxially disposed around the tip 182 and forming an annular path 188 between the elongate tip 182 and the collar 184. The collar 184 includes an inside surface 185 with threads 186 disposed on the inside surface 185.

To assemble the blunt needle component 110 to the syringe barrel 190, the elongate tip 182 of the syringe barrel 190 is inserted into open proximal end 119 of blunt needle component 110 and enters the hub cavity 134 such that the sidewall 132 of the hub connector enters the annular path 188 of the syringe barrel 190. The pair of ribs 137 of the hub connector 130 engage the threads 186 disposed on the inside surface 185 of the collar 184. The syringe barrel 190 or the blunt needle component 110 is rotated such that the threads 186 continue to engage pair of ribs 137, until the syringe barrel 190 and the blunt needle component 110 are engaged and fluid tight communication is established between the opening 197 of the syringe barrel 190 and the open distal end 131 of the hub connector, as shown more clearly in FIG. 2.

It will be understood that syringe barrels with a luer slip configuration (not shown) may also be utilized. Connection of a syringe barrel with a luer slip fitting (not shown) to the hub connector 130 includes inserting the elongate tip of a syringe barrel having a luer slip fitting into the hub cavity 134 and until the outside surface of the elongate tip engages the inside surface 133 of the hub cavity.

After attachment of the syringe barrel 190 to the blunt needle component 110, a predetermined amount of a drug is aspirated into the chamber 196 of the syringe barrel by inserting the distal open end 114 of the blunt needle 112 into a glass ampoule (not shown). A plunger rod (not shown) may be utilized to aspirate the drug into the chamber 196. After the desired amount of the drug is aspirated into the chamber 196 of the syringe barrel 190, the blunt needle 112 is inserted into the inlet 143 of the filter component 140 such that the blunt needle 112 enters the channel 172. In the embodiment shown, the proximally extending wall 164 of the second non-luer connector 160 enters the annular space 124 of the first non-luer connector 120, while the distally extending wall 125 of the first non-luer connector 120 slides over the outside surface 163 of the proximally extending wall 164 of the second non-luer connector 160. The shape of the proximally extending wall 164 and the distally extending wall 125 are configured to form a fluid-tight engagement between the first non-luer connector 120 and the second non-luer connector 160, as shown in FIG. 2. In one or more alternative embodiments, the distally extending wall 125 is shaped to slide over the proximally extending wall 164.

Figure 15:
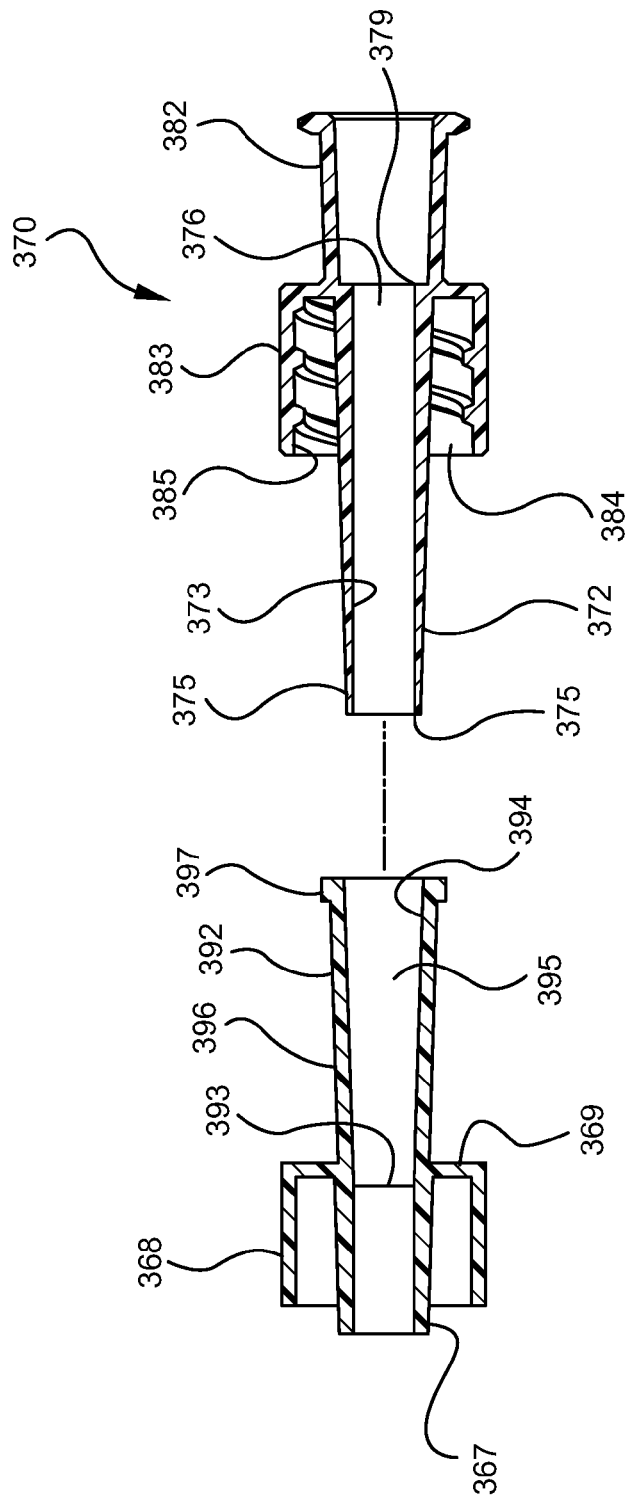
FIG. 15 illustrates a cross-sectional view of the blunt needle component and non-luer component shown in FIG. 14 taken along line 15-15.
Figure 16:
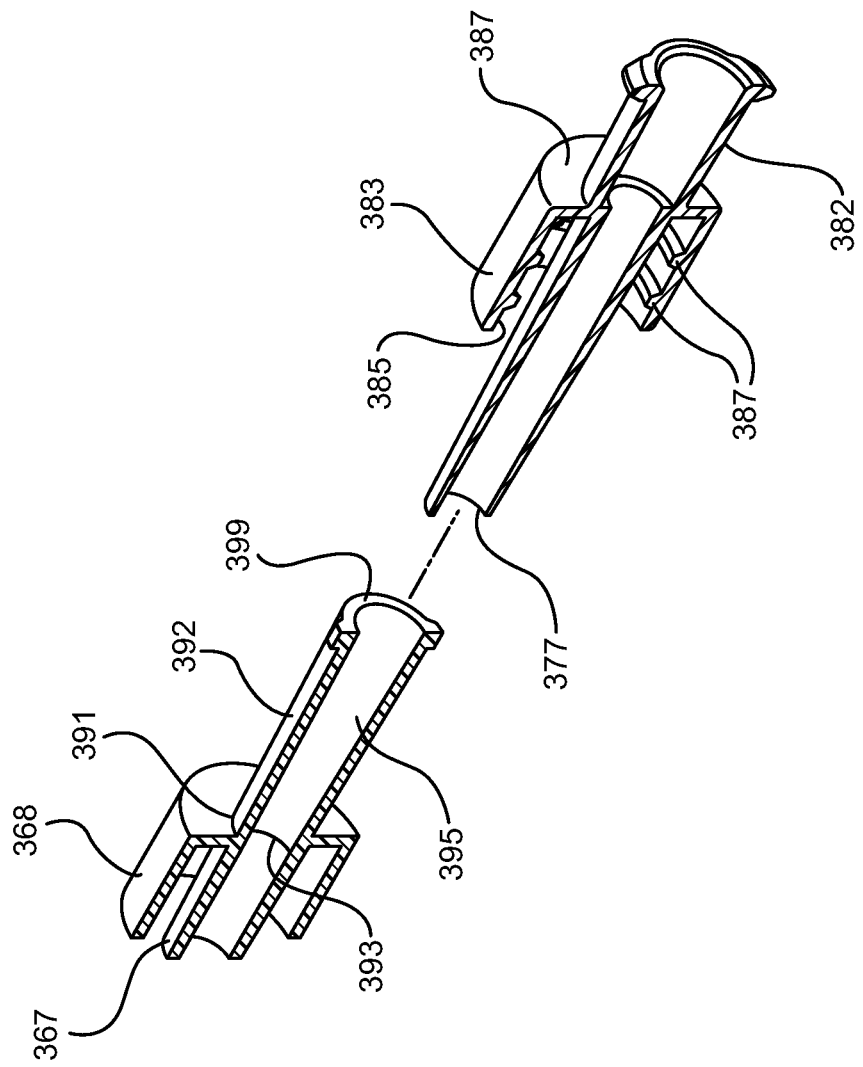
FIG. 16 illustrates a perspective view of the blunt needle component and non-luer component shown in FIG. 15.
Figure 17:
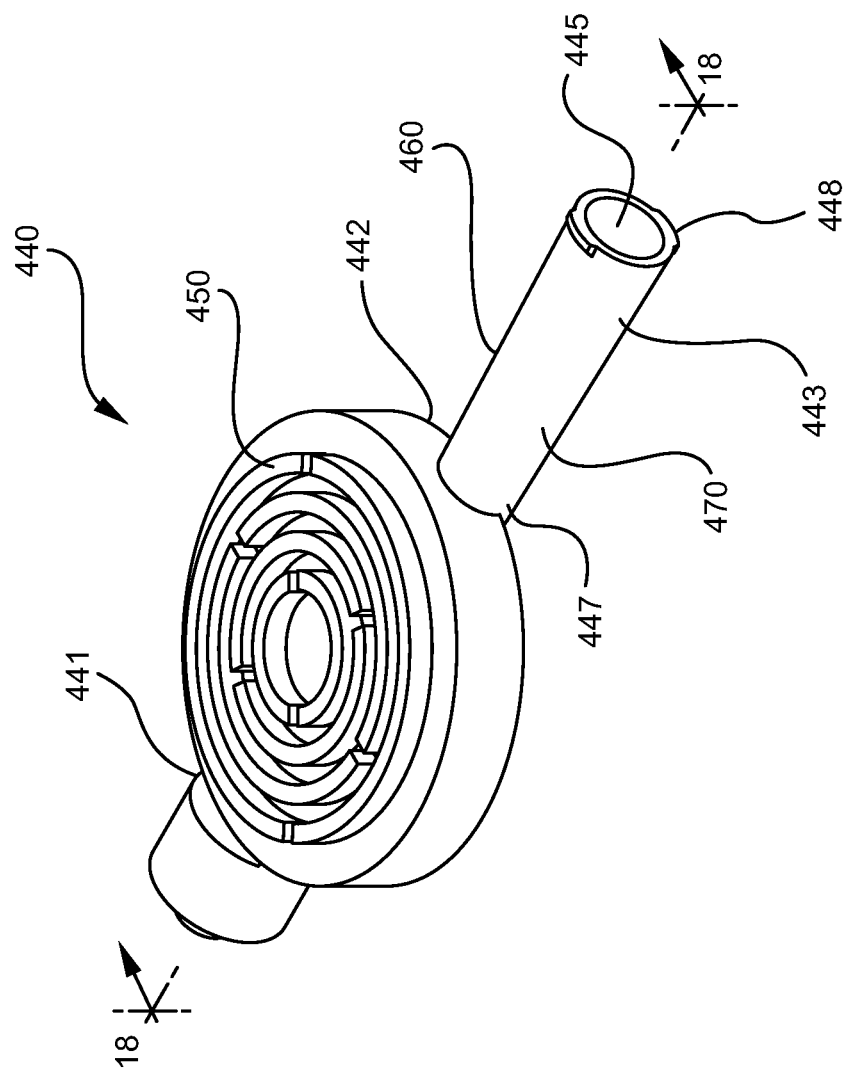
FIG. 17 shows a perspective view of an adapter component according to one or more embodiments.
Figure 18:
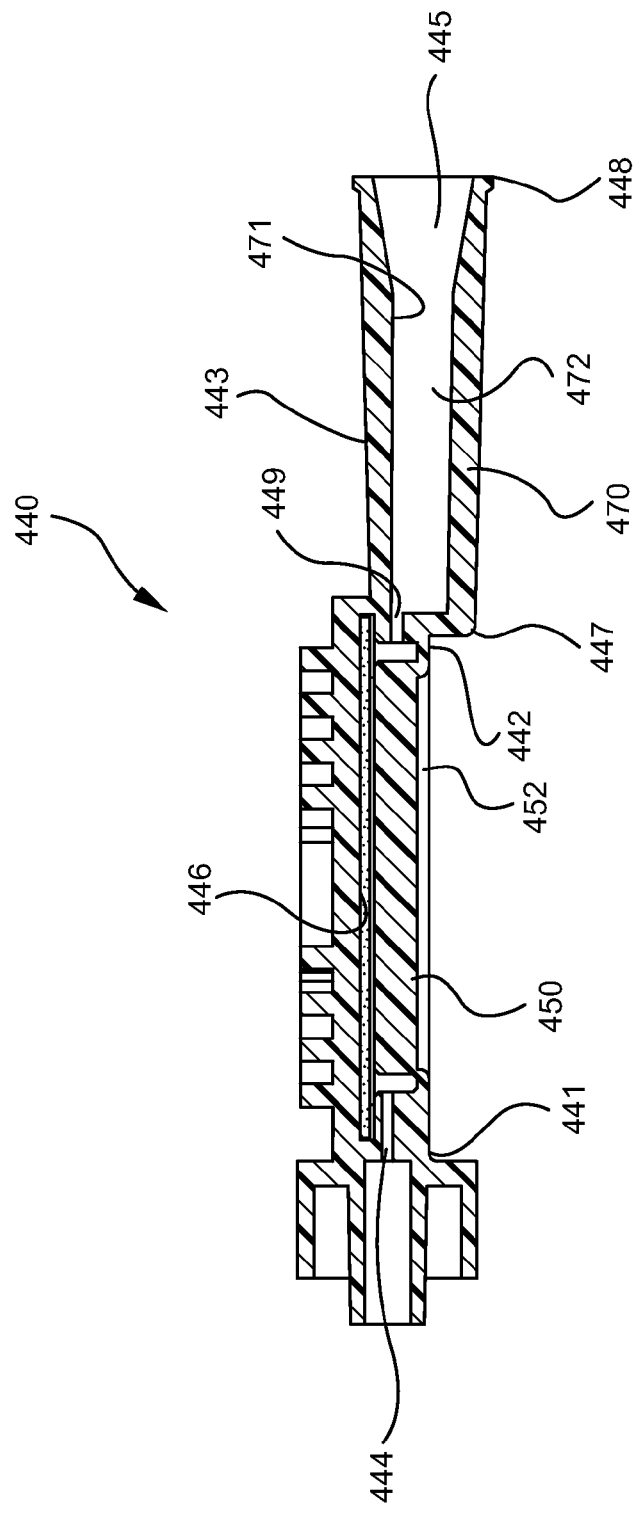
FIG. 18 illustrates a cross-sectional view of the adapter component shown in FIG. 17 taken along line 18-18.

In one or more embodiments, the blunt needle component is free of a non luer connector. In such embodiments, the blunt needle is shaped to form a fluid-tight connection with the second non-luer connector of the filter component. In other words, the blunt needle may provide means for permitting and blocking fluid communication with an incompatible or unintended filter component or a syringe barrel. For example, in one or more embodiments, the blunt needle may have a shape or dimensions that can be characterized as a non-luer shape or dimension. Specifically, the blunt needle may have an outer diameter or outer cross-sectional width that tapers to prevent attachment of the blunt needle to a standard luer connector. In such embodiments, the second non-luer connector has an inner diameter or cross-sectional width that has a corresponding taper or shape to permit fluid-tight connection between the blunt needle and the filter component, as shown in FIGS. 14-16.

Figure 10:
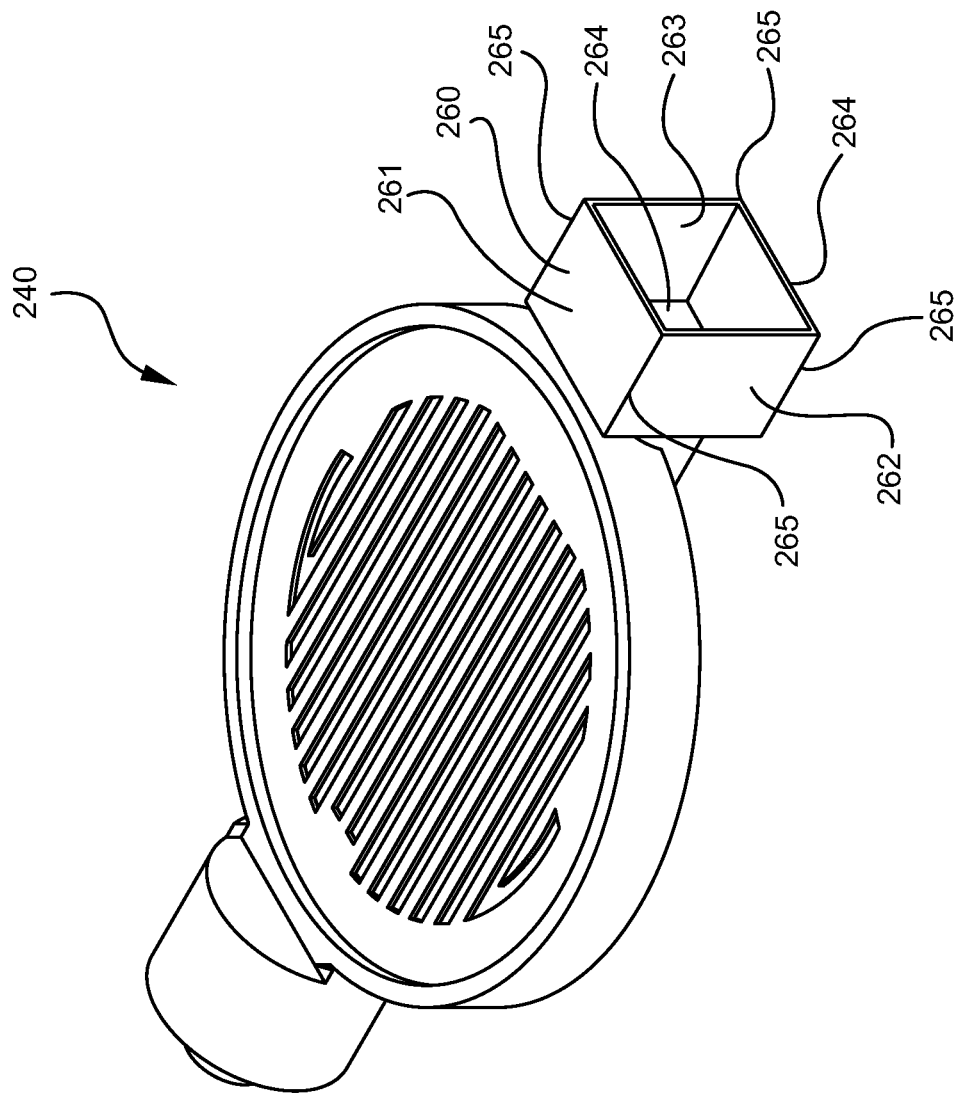
FIG. 10 illustrates a perspective view of a filter component according to one or more embodiments.

In one or more embodiments, the blunt needle may have an oval shaped cross-section to form a fluid-tight connection with a filter component with a second non-luer connector having an oval shaped cross-section, as shown in FIGS. 4-5. In addition, the blunt needle may be shaped to have a square cross-section to form a fluid-tight connection with a filter component with a second non-luer connector having a square shaped cross-section as shown in FIG. 10. Alternatively, the blunt needle may be shaped to have a triangular cross-section to form a fluid-tight connection with a filter component with a second non-luer connector having a triangular shaped cross-section. In such embodiments, the diameter of the blunt needle has a size that enables formation of fluid-tight seal with the inside surfaces of the second non-luer connector of the filter component.

Figure 14:
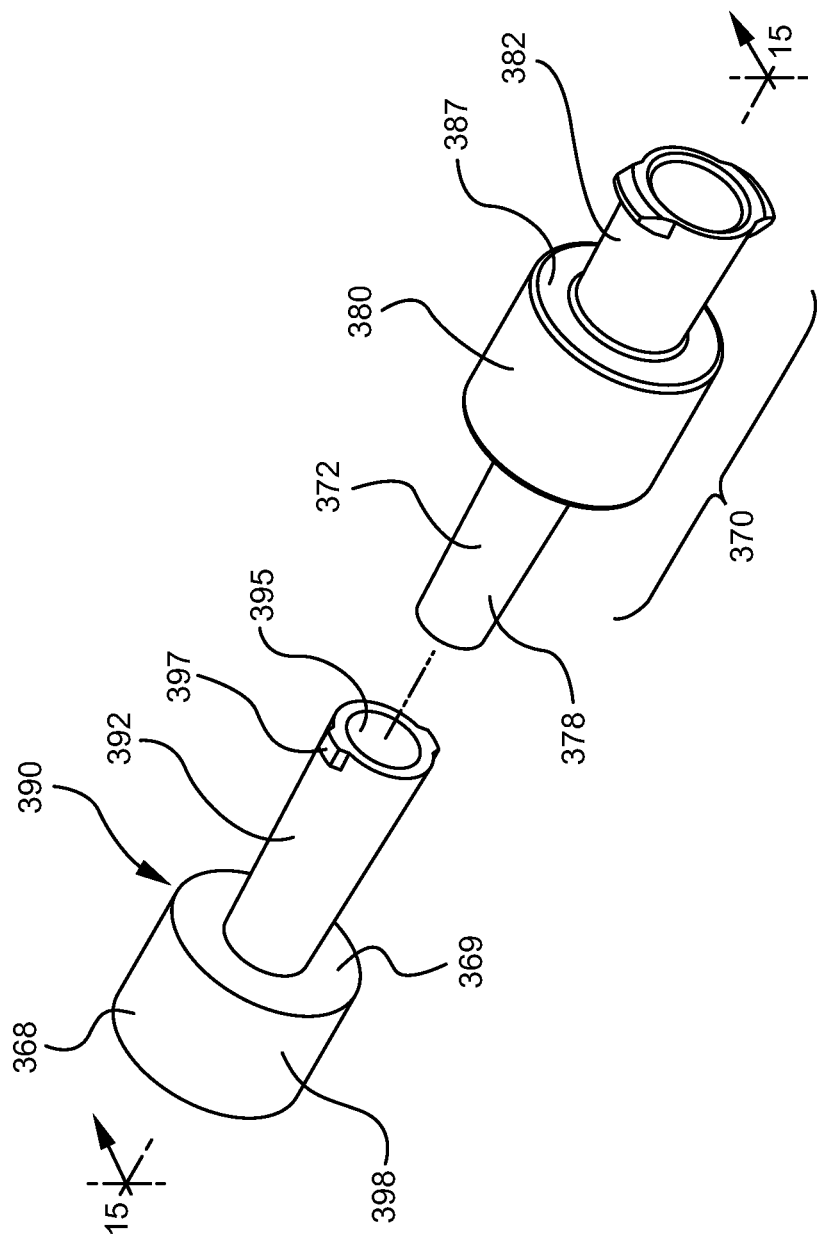
FIG. 14 illustrates a perspective view of a blunt needle component and a non-luer component according to one or more embodiments.

In FIG. 14, the blunt needle component 370 having a non-luer shape or dimension is shown with a second non-luer connector 390 that is shown as a separate piece from the filter component (not shown). The blunt needle component 370 is free of a non-luer connector and, instead includes, a first luer connector 380. The blunt needle component 370 shown in FIGS. 14-16 includes an open distal end 371, an open proximal end 379. The blunt needle component 370 also includes a blunt needle 372 extending from the open distal end 371 to a first luer connector 380. The blunt needle 372 has an elongate shape and includes a distal open end 374 and a proximal open end 376 attached to the first luer connector 380. The blunt needle 372 has a sidewall 378 extending from the proximal open end 376 to the distal open end 374. The sidewall 378 may have an elongate tubular shape or other elongate shape that includes a lumen 377 in the center. The blunt needle 372 may optionally have pores (not shown) through the side wall 378.

The side wall 378 includes an inside surface 373 and an outside surface 375. The outside surface 375 defines a tapered cross-section width that increases from the distal open end 374 to the proximal open end 376 of the blunt needle 372. In one variant, the cross-sectional width of the outside surface 375 of the blunt needle 372 has a may have a cross-sectional width or diameter that increases from about 0.05 inches at or adjacent to the distal open end 374 to a cross-sectional width or diameter of about 0.15 inches at or adjacent to the proximal open end 376. The cross-sectional width of the outside surface 375 at the distal open end 374 may be in the range from about 0.05 inches to about 0.7 inches. The cross-sectional width of the outside surface 375 at the proximal open end 376 may be in the range from about 0.12 inches to about 0.15 inches. In one or more alternative embodiments, the outside surface 375 has a cross-sectional width that permits fluid tight connection within the second non-luer connector 390, which will be described in more detail below. The inside surface 373 of the blunt needle 372 is shown as having a constant cross-sectional width, however, the cross-sectional width of the inside surface 373 may be varied, increase or decrease along the length of the blunt needle 372 in optional embodiments.

As described above with reference to FIGS. 1-13, the blunt needle 372 may has a length sufficient permit fluid-tight engagement between the first luer connector 380 and the second non-luer connector 390. In one or more embodiments, blunt needle 372 has a length that is sufficient to extract a liquid from a glass ampoule. For example, the blunt needle 372 may have a length in the range from about 0.1 to about 1.5 inches, as otherwise described herein. In one or more specific embodiments, the blunt needle has a length in the range from about 0.5 inches to about 1.5 inch. According to a more specific embodiment, the blunt needle 372 has a length in the range from about 0.5 inch to about 1.0 inch. In one or more embodiments, the blunt needle has a length of about 1.0 inch. The blunt needle 372 may be made from plastic material or metal. Examples of suitable plastic material include polypropylene, polycarbonate and combinations thereof. Examples of suitable metals include stainless steel.

The first luer connector 380 is attached to the blunt needle component 370. The first luer connector 380 may include a luer portion at the proximal end 379 in the form of a hub connector 382 and allows attachment of the blunt needle component 370 to standard syringe barrels that include a luer fitting, without the need for additional adapters or other means for enabling the attachment. The hub connector 382 shown in FIGS. 14-16 form part of the proximal open end 376 of the blunt needle 372. The hub connector 382 is shaped to be connected or attached to a fluid source or container, for example a syringe barrel, as shown in FIGS. 1-3. The hub connector 382 shown in FIGS. 6-7 includes a standard luer connector for attachment to a luer lock or luer slip fitting on the fluid source or container. As is understood in the art, a luer lock fitting includes a male conical fitting in a coaxial relationship with an internally threaded collar. A luer slip fitting includes a male conical fitting with no internally threaded collar. The hub connector of the blunt needle components described herein eliminates the need to re-design or alter existing syringe barrels or other fluid containers that utilize a luer fitting. In one or more embodiments, permanent connection mechanisms may be built in the hub connector 382, so that, upon connection of blunt needle component 370 to a syringe barrel or other container, the connection becomes permanent and the blunt needle component 370 and syringe barrel or other container are not detachable. The permanent connection can be realized by welding, which may include ultrasonic welding, gluing, or through design, for example, by incorporating one or more ratchet connector, special threads and other structures known in the art.

The first luer connector 380 is disposed at the proximal open end 376 of the blunt needle 372 and is attached to the hub connector 382. The first luer connector 380 includes a distally extending wall 383 that is coaxially disposed around the blunt needle 372 and extends toward the open distal end 371 of the blunt needle component 370. The distally extending wall 383 defines an annular space 384 between the distally extending wall 383 and the blunt needle 372. A linking portion 387 extends from the hub connector 382 to the distally extending wall 383.

In one or more embodiments, the annular space 384 is configured or shaped to receive the second non-luer connector 390. In one or more alternative embodiments, the distally extending wall 383 is shaped or configured to engage the second non-luer connector 390. In one or more embodiments, the distally extending wall 383 is rotatable around the blunt needle 372 to facilitate connection between the blunt needle component 370 and the second non-luer connector 390 and any other component attached thereto, without rotating the syringe barrel or other container attached to the hub 382. The distally extending wall 383 includes an inside surface 385 with a threaded portion 386 or threads disposed thereon. The threaded portion 386 engages a corresponding surface of the second non-luer connector 390. In one or more embodiments, the inside surface 385 of the distally extending wall may be free of any structure but may be shaped to engage the inside surface of the second non-luer connector 390, which may have a corresponding taper or shape to form a friction fit engagement with the first luer connector 380. In another variant, the distally extending wall 383 may have an outside surface 387 that includes an outwardly extending rib (not shown) for engaging a threaded portion (not shown) on the inside surface of the second non-luer connector. The distally extending wall 383 has standard luer dimensions and/or structure, however, connection of the blunt needle component 370 to an unintended or incompatible filter component or other device is prevented by the non-luer shape and dimension of the blunt needle 372.

The second non-luer connector 390 attaches the blunt needle component 370 to a filter component (not shown). The second non-luer connector 390 includes a proximally extending wall 392 that includes a distal end 391 and a proximal end 399. The proximally extending wall also defines an inlet 393 and includes an inside surface 394 that defines an inlet chamber 395. In one or more embodiments, the inlet chamber 395 receives a portion of the blunt needle component 370 to secure attachment of the second non-luer connector 390 thereto. In the embodiment shown, the inlet chamber 395 may receive the blunt needle 372. The proximally extending wall 392 of the embodiment shown includes an outside surface 396 for engaging the inside surface 385 of the first luer connector 380. Specifically, the outside surface 396 includes an outwardly extending protrusion 397 that engages the threaded portion 386 of the first luer connector 380. The proximally extending wall 392 may be optionally rotatable such that it rotates around the blunt needle 372 during attachment to facilitate the connection between the first luer connector 380 and the second non-luer connector 390 without rotating the filter component (not shown) that may be attached to the second non-luer connector 390. Such rotation of the proximally extending wall 392 would also prevent catheter kinking. The proximally extending wall 392 of the second non-luer connector 390 is shaped to prevent attachment of the filter component (not shown) to an unintended or incompatible fluid source or container. For example, the proximally extending wall 392 of the second non-luer connector 390 is incompatible and cannot be connected to standard syringe that includes a standard luer fitting because it has an inside surface 394 that has a corresponding cross-sectional width to permit connection with the outside surface 375 of the blunt needle 372. Specifically, the inside surface 394 of the second non-luer connector has a cross-sectional width that increases from the distal end 391 to the proximal end 399.

The second non-luer connector includes a standard connector 398 attached at the distal end 391 of the proximally extending wall 392 to connect or attach a filter (not shown) to the second non-luer connector. The standard connector 398 may have a luer fitting, which may include a luer slip or luer lock configuration. In the embodiment shown in FIGS. 14-16, the standard connector 398 includes an conduit 367 extending in the distal direction from the inlet 393 to establish fluid communication between the blunt needle 372 and the filter (not shown) that may be attached to the standard connector 398. The standard connector 398 includes a coaxial wall 368 encircling the conduit 367 and defining a space between conduit 367 and the coaxial wall 368. A bridge portion 369 extends from the distal end 391 of the proximally extending wall 392 to the coaxial wall 368. The coaxial wall 368 may have an inside surface that includes a treaded portion (not shown) for engaging a corresponding structure on a filter (not shown). In the embodiment shown, the conduit 387 has a tapered outside surface for engaging the insides surface in a corresponding structure on a filter (not shown) in a luer slip configuration.

To assemble a blunt needle component that is free of a non-luer connector and utilizes the blunt needle as a non-luer connector to a filter component, the blunt needle is inserted in to the inlet chamber 395 of the second non-luer connector 390. A rotational force is applied to the first luer connector 380 to engage the outwardly extending protrusion 397 on the proximally extending wall 392 and the threaded portion 386 of the first luer connector 380 until the outside surface 375 of the blunt needle 372 forms a fluid tight connection with the inside surface 394 of the second non-luer component 390.

Figure 19:
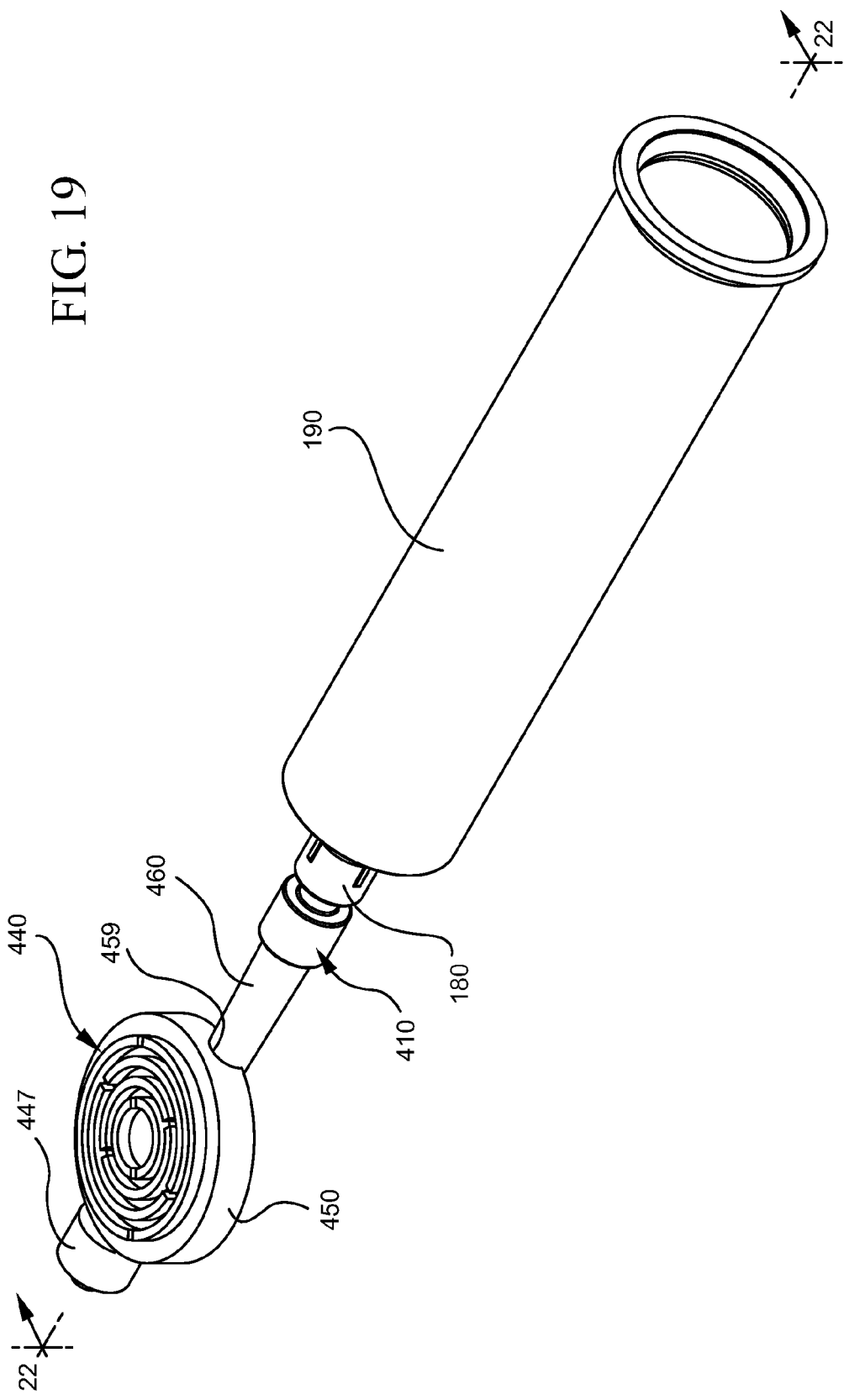
FIG. 19 shows a perspective view of the adapter component of FIG. 17 and a blunt needle component, according to one or more embodiments.

A second aspect of the present invention pertains to an alternative embodiment of the drug delivery device 400. FIGS. 17-22 illustrate the filter component 440 that includes a proximally extending second non-luer connector 460. FIG. 19 illustrates the drug delivery device 400 assembled with syringe barrel 190 having a luer lock fitting 180, as described above. The drug delivery device 400 includes a blunt needle component 410 with a first non-luer connector 420 including distally extending wall 425 with a threaded inside surface 426, for engaging the second non-luer connector 460. The distally extending wall 425 is coaxially disposed around a blunt needle 412 and forms an annular space 424 between the distally extending wall 425 and the blunt needle 412. The blunt needle component 410 includes a hub connector 430 attached to the first non-luer connector 420 and includes a luer fitting formed by a sidewall 432 that includes an inside surface defining a hub cavity for receiving a luer lock or luer slip fitting. The distally extending wall 425 is attached to the hub connector 430 by a connecting portion 428.

Figure 20:
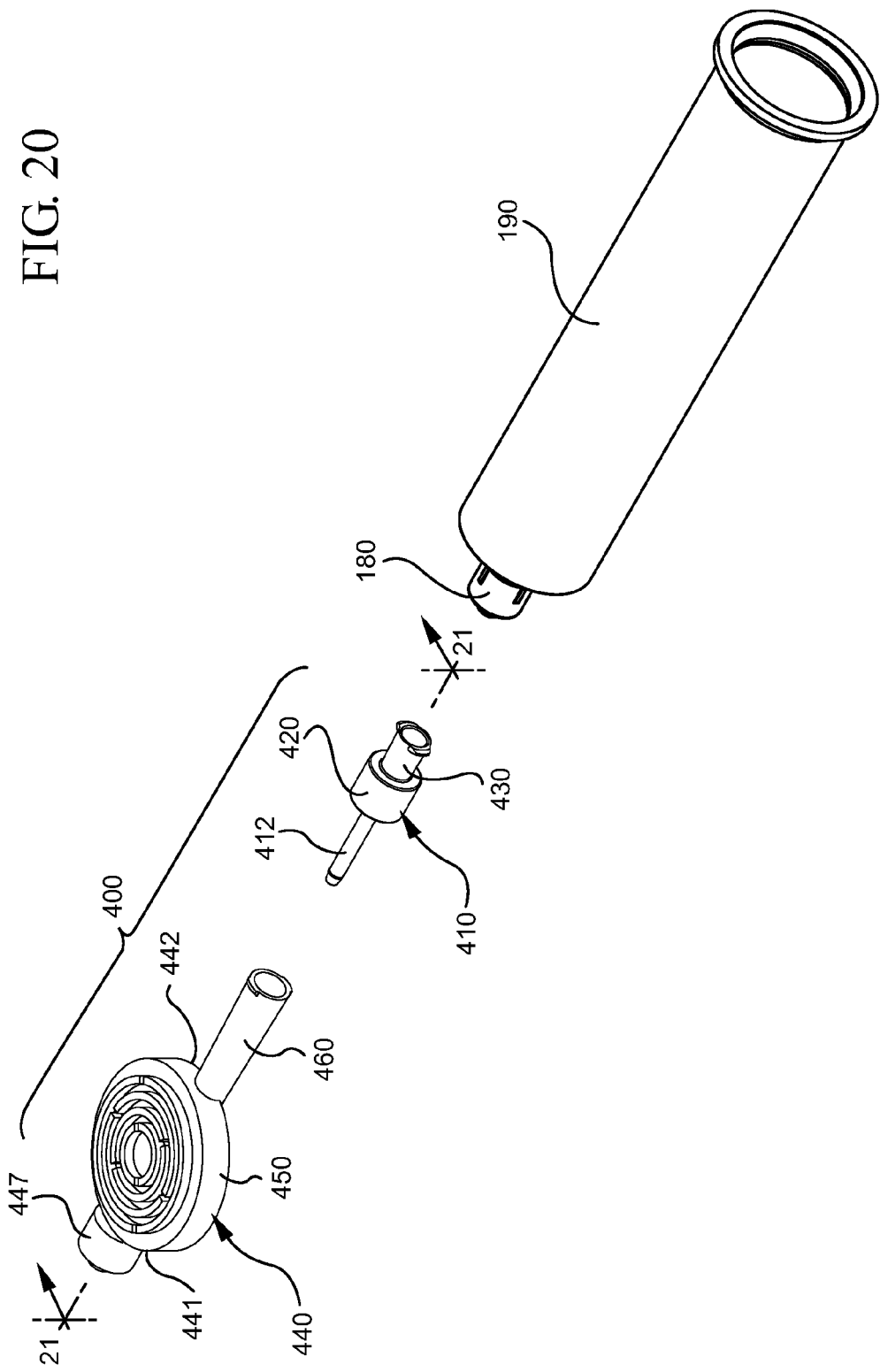
FIG. 20 illustrates a cross-sectional view take along line 20-20 of the adapter component and the blunt needle component shown in FIG. 19.
Figure 21:
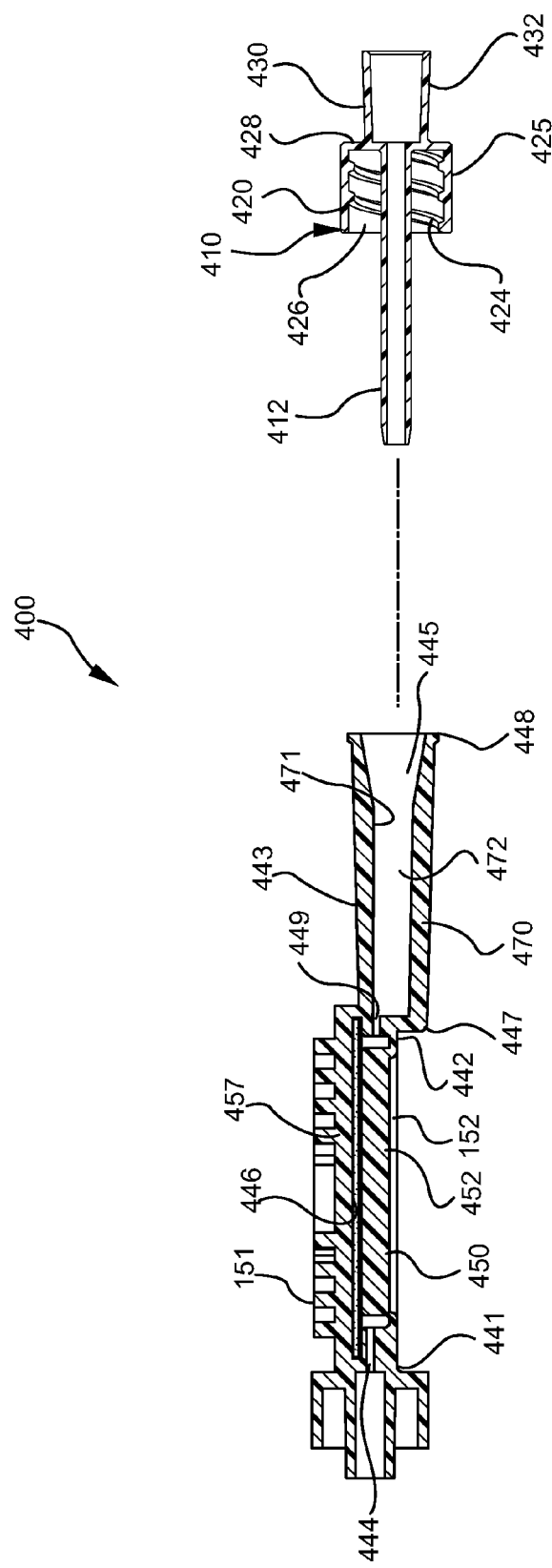
FIG. 21 shows an exploded cross-sectional view of a filter component including a luer connection, an adapter component and a blunt needle component according to one or more embodiments, with a perspective view of a syringe barrel.

As more clearly shown in FIGS. 20-21, the filter component 440 includes a distal end 441 and a proximal end 442 and a filter housing 450 extending from the distal end 441 to the proximal end 442. The filter component 440 also includes an inlet 443 disposed at the proximal end 442 and an outlet 444 disposed at the distal end 42. The outlet 444 may include a luer fitting 477 as discussed above with reference to embodiments according to the first aspect of the present invention.

The inlet 443 includes an opening 445 to a filter cavity 446 450 so the inlet 443 and the filter cavity 446 are in fluid communication. The distal end 447 includes an aperture 449 allowing fluid communication between the inlet 443 and the filter cavity 446. The inlet 443 includes a distal end 447 disposed adjacent to the proximal end 442 of the filter component 440 and a proximal end 448. Specifically, the distal end 447 of the inlet is attached to the filter housing 450 at a cut out portion 459 in the filter housing 450.

The inlet 443 is shaped to receive the blunt needle 412. The inlet 443 shown in FIGS. 17-18 has an elongate tubular shape to receive the blunt needle 412 and extends proximally from the filter housing 450. Specifically, the inlet 443 includes an enclosed tubular body 470 having an inside surface 471 defining a channel 472. The opening 445 is disposed at the distal end 441 of the inlet 443.

Figure 22:
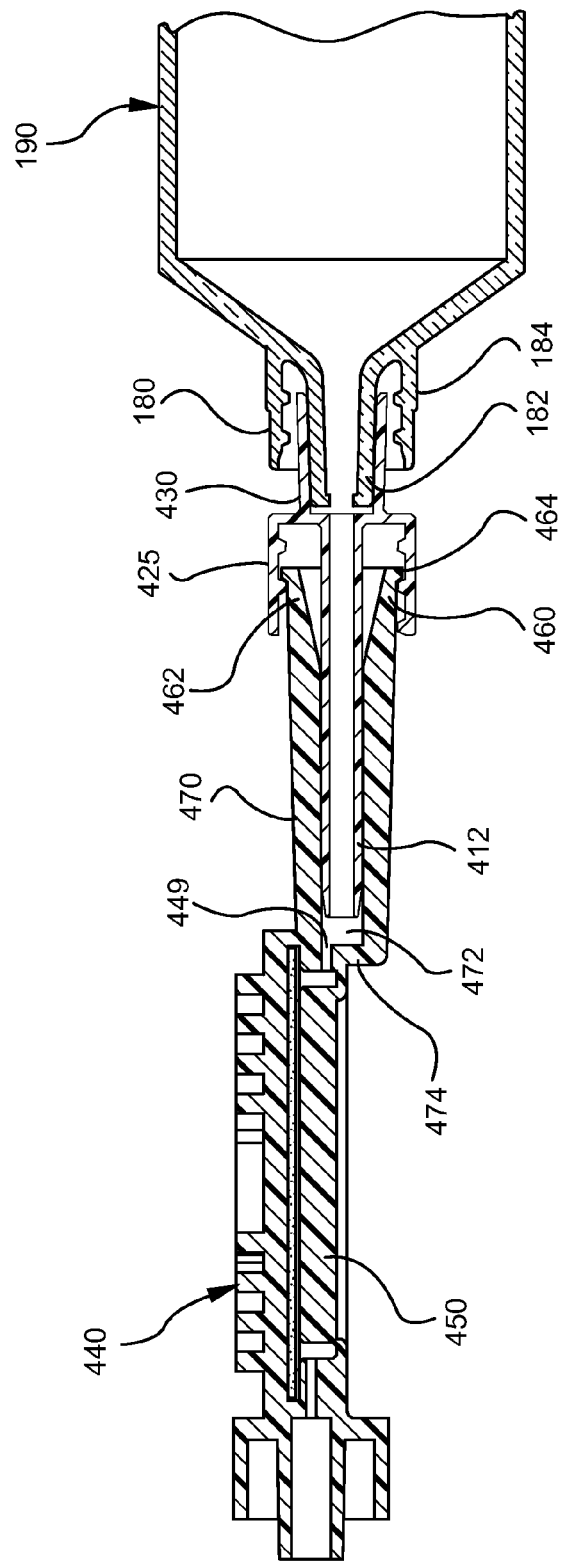
FIG. 22 illustrates a perspective view of an adapter component and blunt needle component according to one or more alternative embodiments.
Figure 23:
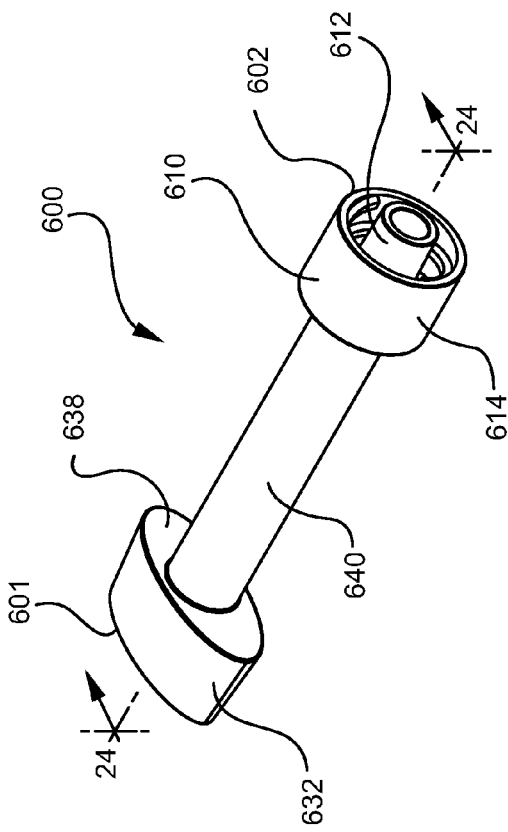
FIG. 23 illustrates a perspective view of an adapter component and blunt needle component according to one or more embodiments.

In the embodiment shown in FIGS. 20-22, the inlet 443, including the enclosed tubular body 470 extends from the filter housing 450 in the proximal direction. The inlet 443 is disposed along the same plane as the filter housing 450 in the embodiments shown. In one or more embodiments, the inlet 443 may be disposed at an angle between 0 degrees to 90 degrees from the filter housing 450 to facilitate connection and injection when the filter component 440 is taped or otherwise attached to a patient body.

The inside surface 471 of the enclosed tubular body 470 may have a cross-sectional width or diameter that permits formation of a fluid tight seal with the outside surface 415 of the blunt needle 412. In one or more embodiments, the inside surface 471 may have a varying cross-sectional width or diameter that corresponds to a varying cross-sectional width or diameter of the outside surface 415 of the blunt needle 412. The opening 445 is disposed at one end of the enclosed tubular body 470, while the other end of the enclosed tubular body 470 is closed by a closed end 474.

At least portion of the inlet 443 includes the second non-luer connector 460. The second non-luer connector 460 may be disposed at the proximal end 448 of the inlet 443. Specifically, a portion of the enclosed tubular body 470 may be contoured to prevent connection of the filter component 440 to in having a cross-section, which is incompatible or prevents the attachment of luer connectors, which have circular openings, are conically shaped conical and/or meet the definition of ISO 594 parts 1 and 2. For example, in the embodiments shown in FIGS. 17-22, the enclosed tubular body 470—has a cross-sectional width that is smaller or less than the cross-sectional width of luer connectors. In the embodiment shown, the proximal end 452 of the inlet may include an engaging portion 462 for securing the first non-luer connector 420. One example of the engaging portion 462 is shown in FIGS. 17-22 as a pair of radially outwardly extending tabs 464 which engage the threaded inside surface 426 of the first non-luer connector 420. The channel 472 adjacent to the proximal end 448 of the inlet may be shaped to receive a portion of the blunt needle component 410 to secure attachment of the filter component 440 thereto.

The portion of the enclosed tubular body 470 forming the second non-luer connector 460 may have threads (not shown) disposed on the outside surface or inside surface thereof. The portion of the enclosed tubular body 470 may be optionally rotatable such that it rotates around the blunt needle 412 during attachment to facilitate the connection between the first non-luer connector 420 and the second non-luer connector 460 without rotating the filter component 440. Such rotation of the enclosed tubular body 470 would also prevent catheter kinking. In contrast to the second non-luer connector 160 shown in FIGS. 1-13, opening 445 of the inlet 443 does not extend into the filter housing 450.

As discussed above with respect to the first aspect of the present invention, the first non-luer connector 420 and second non-luer connector 460 may have oval, square, triangular or other shaped cross-sections to reduce misconnections. Other structural features for reducing misconnection or unintended connections to syringe barrels, route-accessing devices and the like using luer fittings discussed above with respect to the first aspect may also be incorporated in the first non-luer connector 420 and second non-luer connector 460 of the second aspect of the present invention. In addition, means for preventing reuse of the blunt needle 412 described herein may also be incorporated to embodiments according to the second aspect of the present invention.

To assemble the filter component 440 shown in FIGS. 17-22, the blunt needle 412 is inserted into the inlet 443 of the filter component 440 such that the blunt needle 412 enters the channel 472. The threaded inside surface 426 of the first non-luer connector 420 engages pair of radially outwardly extending tabs 464, while the enclosed tubular body 470 of the second non-luer connector 460 slides into the annular space 424 between the blunt needle 412 and the distally extending wall 425. The tubular body 470 or the distally extending wall 425 are rotated with respect to each other so that the pair of radially outwardly extending tabs 464 engages the threaded inside surface 426 of the first non-luer connector 420 and forms a fluid-tight engagement between the first non-luer connector 220 and the second non-luer connector 460, as shown in FIG. 22. In one or more alternative embodiments, the inside surface of the inlet 443 may include a threaded surface (not shown) to engage with a corresponding structure on the outside surface of the blunt needle 412 (not shown).

A drug delivery device 500 according to a third aspect of the present invention is shown in FIGS. 23-27. Embodiments according to the third aspect incorporate an adapter 600 for use with a filter component 540 and a blunt needle component 510, which include luer connectors and no non-luer connectors, of the drug delivery device 500. Such embodiments eliminate the need to change existing devices and can be used with existing components of the drug delivery device 500, without replacing such components. In one or more embodiments, two adapters 600 may utilize to form two corresponding non-luer fittings on the drug delivery device 500. Specifically, one adapter can be attached to a syringe barrel (not shown) and a second adapter may be attached to the filter component 540 such that both the filter component 540 and the syringe barrel (not shown) have no-luer fittings to prevent accidental connection of unintended or incompatible devices to either the filter component 540 or the syringe barrel (not shown).

For illustration, the adapter 600 is shown with a blunt needle component 510 that includes a blunt needle 512 including a first non-luer connector 520. The filter component 540 shown in FIGS. 23-27 includes an inlet 543 with a second luer connector 560. The blunt needle component 510 includes a hub connector 530 for attaching the blunt needle component 510 to a luer fitting as otherwise described herein. The second connector 560 shown in the embodiment of FIGS. 23-27 includes a luer fitting 562.

It will be understood that the blunt needle component may include a luer fitting, while the filter component includes a non-luer fitting and the luer portion of the adapter may be attached to the luer fitting of the blunt needle component and the non-luer portion of the adapter may be attached to the non-luer fitting of the filter component.

Figure 24:
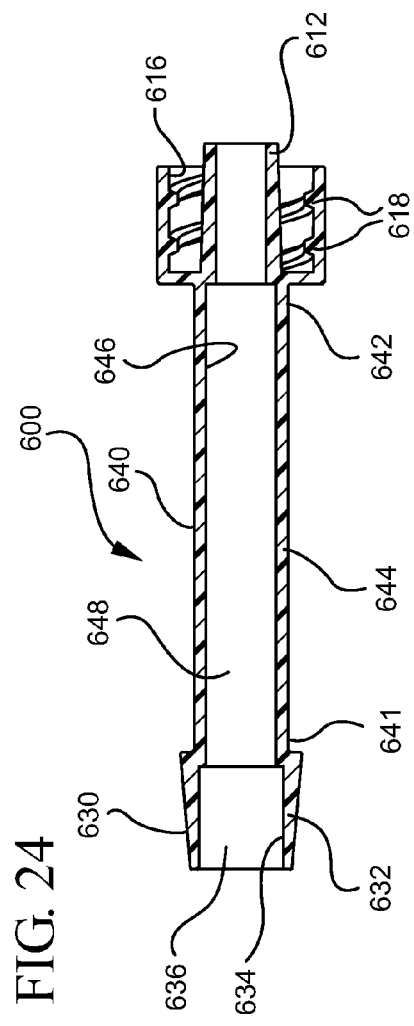
FIG. 24 illustrates a perspective view of a filter component with an integrated connector according to one or more embodiments.

As shown more clearly in FIG. 24, the adapter 600 includes an open distal end 601 and an open proximal end 602. One of the distal end 601 and the proximal end 602 includes a luer portion 610, while the other of the distal end 601 and the proximal end 602 includes a non-luer portion 630. A main body portion 640 extends between the luer portion 610 and the non luer portion 630 and includes a distal end 641 and a proximal end 642. The main body portion 640 includes a hollow tube 644 extending from the distal end 641 to the proximal end 642. The hollow tube 644 has inside surface 646 defining a hollow interior 648 in fluid communication with the open distal end 601 and the open proximal end 602 of the adapter 600.

The luer portion 610 shown in FIGS. 23-27 includes a luer lock fitting including a male conical fitting 612 extending outwardly and a threaded collar 614 coaxially disposed around the male conical fitting 612. The threaded collar 614 including an inside surface 616 with threads 618 disposed thereon. The hub connector attachment to a luer lock or luer slip fitting may also be incorporated into the luer portion 610.

The non-luer portion 630 in the embodiments shown includes an extending wall 632 connected to the main body portion 640 by a linking wall 638 disposed perpendicularly to the main body portion 640 and extending radially outwardly therefrom. The extending wall 632 extends toward the distal or proximal direction from the main body portion 640, depending on the orientation of the adapter 600. The extending wall 632 includes an inside surface 634 that defines a non-luer chamber 636. In the embodiment shown in FIGS. 23-27, the non-luer chamber 636 receives the first non-luer connector 520 of the blunt needle component 510 to secure attachment of the blunt needle component 510 to the filter component 540, as will be described in more detail below. When the luer portion 610 of the adapter 600 is attached to the luer fitting 562 of the filter component 540, the non-luer portion 630 is shaped to prevent attachment of the filter component 540 to an unintended or incompatible fluid source or container. For example, the shape, size or configuration of the extending wall 632 is incompatible and cannot be connected to standard syringes or route-accessing devices that include a standard luer fitting. In the embodiments shown in FIGS. 20-23, the extending wall 632 of the non luer portion 630 has an oval shape to engage the corresponding oval shape of the filter component 540.

In use, the adapter is attached to one of the filter component 540 or the blunt needle component 510 such that the non luer portion 620 is free and not engaged to any portion. Thereafter, the other of the filter component 540 and the blunt needle component 510, having a non luer fitting would be attached to the non luer portion 620.

Figure 28:
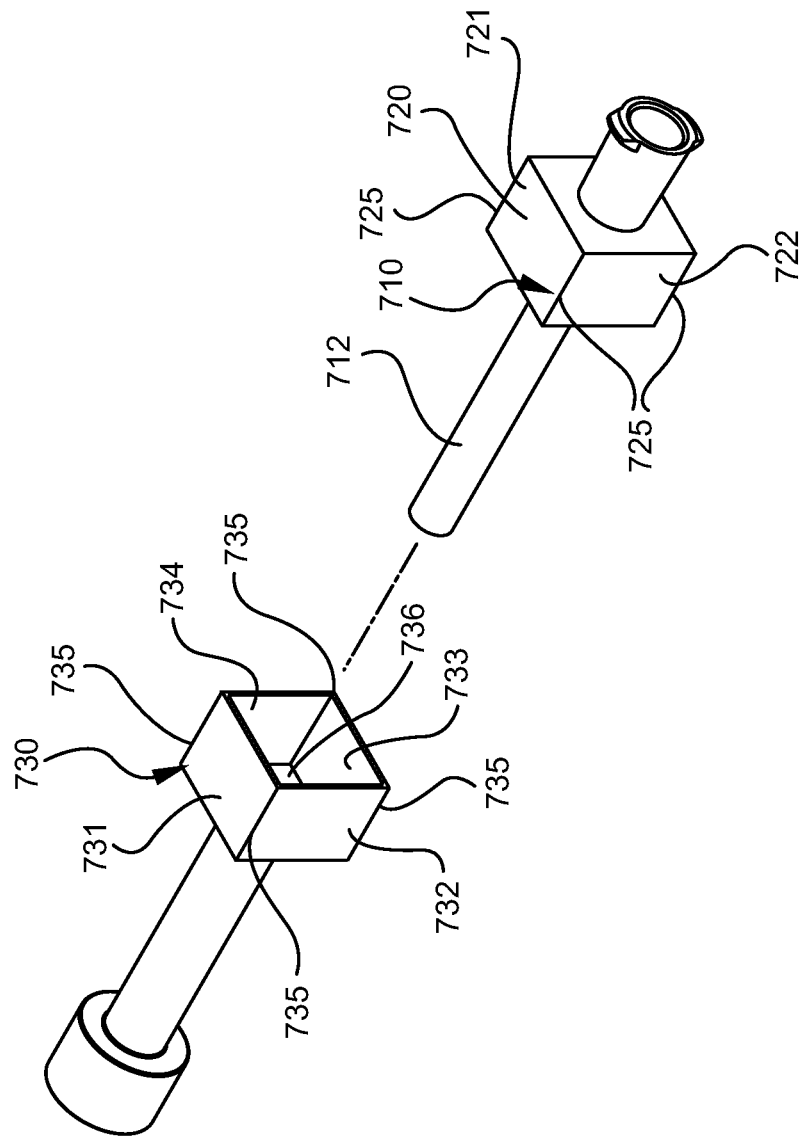
FIG. 28 shows a cross-sectional view of the filter component and blunt needle component of FIG. 27 taken along line 28-28.
Figure 29:
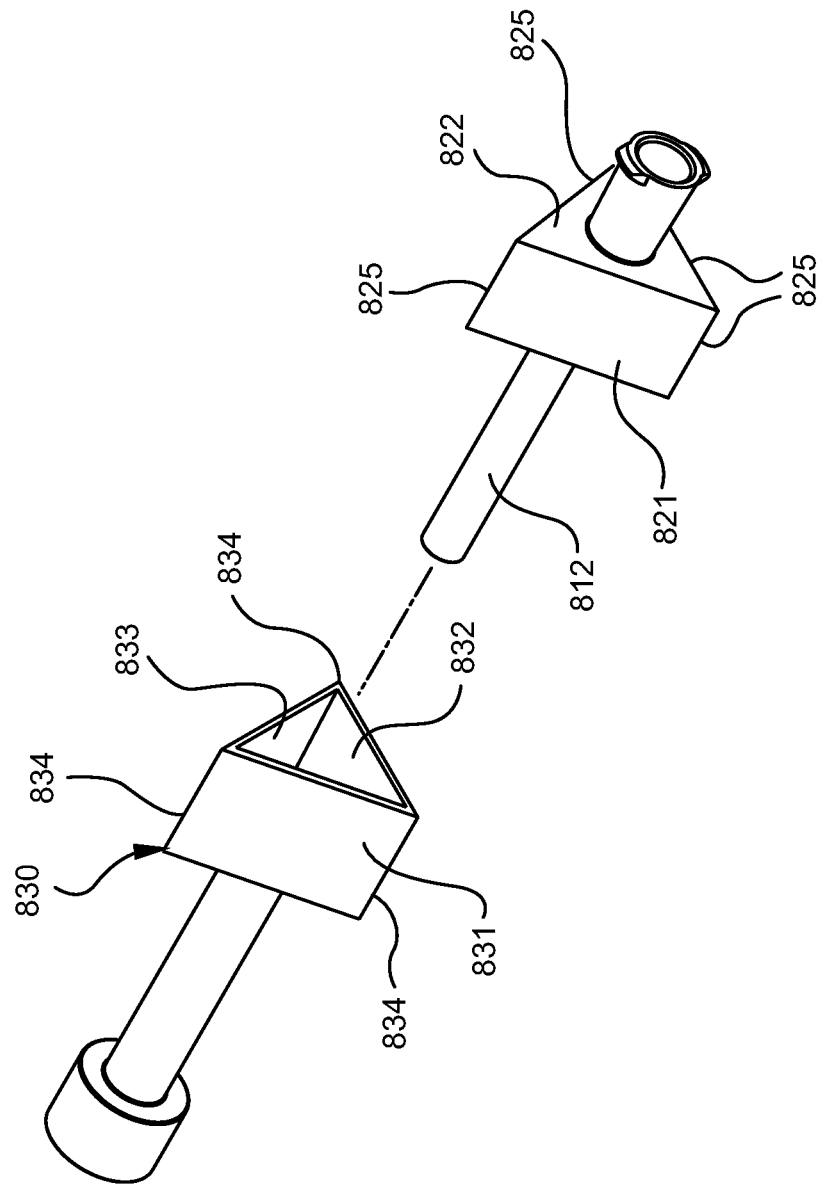
FIG. 29 shows an partial cross-sectional view of the filter component, blunt needle component and syringe barrel of FIG. 26 taken along line 29-29.

Alternative embodiments of the non luer portion are shown in FIGS. 28 and 29. In FIG. 28, the non luer portion 730 of the adapter 700 has a square cross-section and includes a bridge portion 734 connecting the non luer portion 730 to a blunt needle component. The non-luer portion 730 includes four walls 731, 732, 733, 734, each having at least two side edges 735 each, wherein all four walls are joined by at least two side edges 735 to each other to form a hollow square configuration having four sides that surround a blunt needle 712 in which a bridge portion 736 forms part of a fifth side. The blunt needle component 710 shown in FIG. 28 includes a first non-luer connector 720 having a corresponding square cross-section with a corresponding linking portion 724. The second non-luer connector 720 includes four walls 721, 722, 723 (not shown), 724 (not shown) each having a side edge 725, wherein all four walls are joined at least two side edges 725 to each other to form a hollow square configuration having four sides that form a hollow square cross-section, in which the linking portion 727 forms part of a fifth side.

FIG. 29 shows another embodiment of non luer portion 830 if adapter 800 having a triangular cross-section and includes a linking portion 834. The non-luer portion 830 includes three walls 831, 832, 833, each having at least two side edges 835 each, wherein all three walls are joined by at least two side edges 835 to each other to form a hollow triangular configuration having three sides that surround a blunt needle 812 in which a bridge portion (not shown) forms part of a fourth side. FIG. 29 also illustrates a blunt needle component 810 with a first non-luer connector 820 having a non luer portion 822 having a corresponding triangular cross-section. The second non-luer connector 820 includes four walls 821, 822, 823 (not shown) each having a side edge 824, wherein all four walls are joined at least two side edges 825 to each other to form a hollow square configuration having four sides that form a hollow triangular cross-section, in which the linking portion 827 forms part of a fourth side.

Alternative embodiments of the adapter may include structural features as described above with respect to the filter component and the blunt needle component for preventing misconnection and for preventing reuse the blunt needle.

In one or more embodiments, the adapter 600 may include a valve (not shown). The valve may be a one-way or check valve that requires application of a force on the valve in the distal direction to open the valve and to permit access to the filter component. Specifically, such a valve may include a ball valve, a flap valve, or other known one-way valves known in the art. The valve may be spring-loaded (not shown). To gain access to the filter component 540 and the catheter connector (not shown), the blunt needle 112 would need to be inserted into the adapter 600 and exert a force on the valve in the distal direction to open the valve. The opening of the valve would permit the blunt needle component 510 to form a fluid tight engagement and allow fluid communication between the syringe or other fluid container attached to the blunt needle component 510 and the filter component 540. In such embodiments, the valve (not shown) would be disposed within the main body portion 640 or within the adapter so that it could only be opened by a blunt needle 512, as described herein, having a sufficient length. In such embodiments, standard luer slip tips, which typically are 0.4 inches in length, would not be able to open the valve.

In one or more alternative embodiments, the valve (not shown) may include a split septum (not shown). The split septum may be attached to the proximal end 602 of the adapter 600. The split septum may be swabable and provides a barrier to microbials and other contaminants. To gain access to the filter component 540 and the catheter connector (not shown), the blunt needle 512 would need to be inserted into the adapter 600 and exert a force on the split septum in the distal direction to open the split septum. The opening of the split septum would permit the blunt needle component 510 to form a fluid tight engagement and allow fluid communication between the syringe or other fluid container attached to the blunt needle component 510 and the filter component 540.

Figure 27:
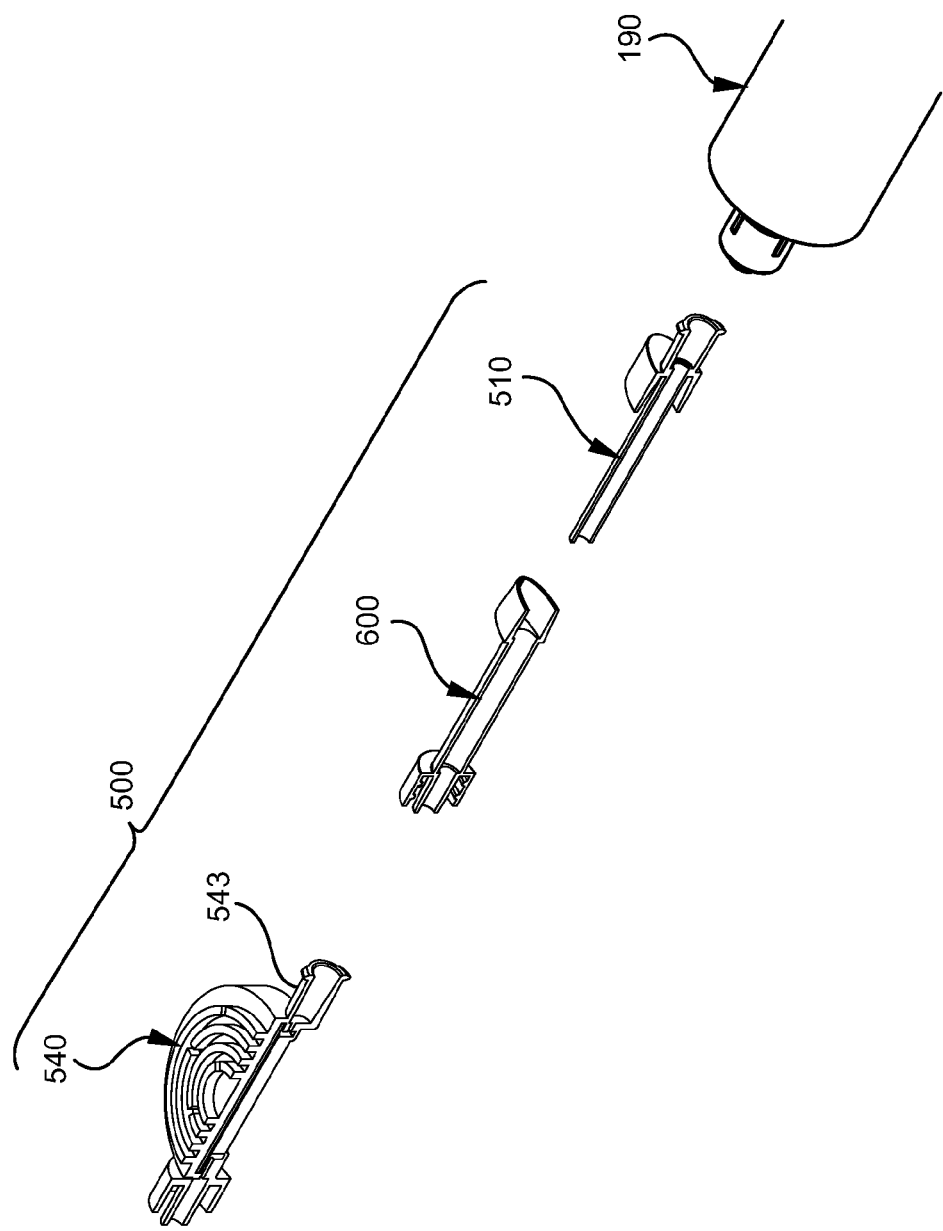
FIG. 27 shows an exploded view of the filter component, blunt needle component and syringe barrel of FIG. 26.

A fourth aspect of the present invention pertains to a pair of adaption connectors 900 which may be attached to luer fittings of blunt needle components, filter components, syringe barrels and other drug delivery devices to form a non-luer fitting to reduce misconnection. As shown in FIGS. 27 and 28, the adaption connectors 900 include a first piece 910 and a second piece 940 which are shaped to connect to one another. Each of the first piece 910 and the second piece 940 has a non luer fitting and a luer fitting that may be attached to the filter components, blunt needle components, and syringe barrels described herein.

The first piece 910 shown in FIGS. 30 and 31 includes an open first end 911 and an open second end 912. The first piece 910 also includes a first portion 914 disposed adjacent to the open first end 911, a main body 916 disposed adjacent to the first portion 914, and a second portion 918 extending from the main body 916 to the open second end 912. The first portion 914 of the first piece 910 includes a standard luer fitting 920. In the embodiments shown in FIGS. 30-31, the standard luer fitting 920 includes a luer lock fitting with a male conical fitting 922 surrounding the open first end 911 and a collar 924 having an inside surface 926 and threads 928 disposed thereon. The first portion may optionally include a luer slip fitting (not shown). The second portion 918 includes a non-luer fitting 930 including a extending wall 932 that extends from the main body 916 and surrounds the open second end 912. The extending wall 932 includes an inside surface 934 that defines a chamber 936 and an outside surface 935. In one or more embodiments, the inside surface 934 and/or the outside surface 935 engages a portion of the second piece 940 to secure attachment of the first piece 910 and the second piece 940, and the components attached thereto, as will be described in more detail below. The extending wall 932 may include threads on the inside surface 934, the outside surface 935 or both the inside surface 934 and the outside surface 935. The extending wall 932 may be optionally rotatable such that it rotates around the second piece 940 during attachment to facilitate the connection.

The extending wall 932 of the second portion 918 is shaped to prevent attachment of the filter component or blunt component to an unintended or incompatible fluid source or container. For example, the extending wall 932 is shaped or has the structural features rendering it incompatible with standard syringe or route accessing devices that include a standard luer fitting. In the embodiments shown in FIGS. 27-28, the extending wall 932 has an oval cross-section that is incompatible with or prevents the attachment of luer connectors, which have circular openings, are conically shaped conical and/or meet the definition of ISO 594 parts 1 and 2. It will be understood that the shape and configuration of the extending wall may incorporate other structural features described herein to reduce misconnection.

The second piece 940 shown in FIGS. 30-31 includes an open first end 941 and an open second end 942. The second piece 940 also includes a first portion 944 disposed adjacent to the open first end 941, a main body 946 disposed adjacent to the first portion 944, and a second portion 948 extending from the main body 946 to the open second end 942. The first portion 944 of the second piece 940 includes a standard luer fitting 950. In the embodiments shown in FIGS. 30-31, the standard luer fitting 950 includes a hub connector 952 for attachment to a luer lock or luer slip fitting, disposed on the first piece 910. The hub connector 952 includes sidewall 953 extending from the open second end 942 to the main body 946. The sidewall 953 includes an inside surface 954 defining a hub cavity 955 for receiving a luer lock or luer slip fitting. The inside surface 954 of the sidewall 953 is may be tapered to have a cross-sectional width that increases from the open second end 942 to the main body 946. The tapered shape of the sidewall 953 allows the inside surface 954 of the hub connector to engage the male conical fitting of a luer slip fitting. The hub connector 952 includes an outside surface 956 and a radially outwardly extending portion 957 disposed on the outside surface 956 that engages the threaded internal collar of a luer lock fitting. The radially outwardly extending portion 957 may include at a pair of ribs 959, as shown in FIGS. 30-31. In one or more embodiments, the radially outwardly extending portion 957 may include a single rib (not shown), or, in one or more specific embodiments, the radially outwardly extending portion 957 may include a peripheral lip (not shown) that is disposed on the outside surface 956 along the circumference of the hub connector 952. The second portion may optionally include a luer slip fitting (not shown).

The second piece 940 of the second piece includes a non-luer fitting 960 including a extending wall 962 that extends from the main body 946 and includes an inside surface 964 that defines an chamber 966. In one or more embodiments, the chamber 966 engages a portion of the first piece 910 to secure attachment of the first piece and the second piece, and the components attached thereto, as will be described in more detail below. The extending wall 962 may be optionally rotatable such that it rotates around the first piece during attachment to facilitate the connection. The extending wall 962 of the second piece 940 is shaped to prevent attachment of the second piece and the filter component or blunt component that may be attached thereto to an unintended or incompatible fluid source, container or route accessing device. For example, the extending wall 962 is shaped or has the structural features rendering it incompatible with standard syringe or route accessing devices that include a standard luer fitting. In the embodiments shown in FIGS. 3-31, the extending walls of the first piece and the second piece have an oval cross-section that is incompatible with or prevents the attachment of luer connectors, which have circular openings, are conically shaped conical and/or meet the definition of ISO 594 parts 1 and 2. It will be understood that the shape and configuration of the extending wall may incorporate other structural features described herein to reduce misconnection.

In one or more embodiments, the one or both adapter connectors may include a valve (not shown), as otherwise described herein. The valve may include a split septum valve and may be disposed within one or both adapter connectors so that it could only be opened by a blunt needle, as described herein, having a sufficient length. In such embodiments, standard luer slip tips, which typically are 0.4 inches in length, would not be able to open the valve.

The embodiments of the drug delivery devices and adapters described herein may be used for continuous, intermittent, or single-shot or single dose drug delivery. Examples of continuous anesthesia drug delivery applications include including continuous epidural combined spinal epidural procedures and peripheral nerve block procedures. Examples of single-shot anesthesia drug delivery applications including spinal procedures, single-shot epidural procedures, spinal epidural procedures and peripheral nerve block procedures. Single-shot anesthesia drug delivery applications may also include applications in which the filter component is attached to a spinal needle or other anesthesia needles. The embodiments according to the first aspect of the invention may also be utilized in continuous or single-shot intravenous delivery applications.

The embodiments described herein reduce non-intended route connections because, for example, when the blunt needle component is attached to a syringe barrel or other fluid container containing a drug, the drug cannot be applied to the non-intended route due to the presence of the blunt needle and the non-luer portion of the first non-luer connector. In embodiments which utilize the adapter connectors, the non-luer connection fitting of one of the first or second adapter connectors attached to the blunt needle component would further prevent application to a non-intended route. In addition, when the filter component is attached to a route-accessing device, the drug from another drug containing device cannot be readily applied to that route-accessing device because the second non-luer connector of the filter component would prevent connection between the drug containing device with a luer opening and the filter component. In embodiments which utilize an adapter 600, the non-luer portion 630 attached to the filter component would prevent connection between the drug containing device using a luer opening and the filter component. In addition, in embodiments which utilize the adapter connectors, the non-luer portion of one of the first or second adapter connectors would also prevent connection between a drug containing device using a luer opening and the filter component.

These means for preventing connection between incorrect drug containing devices to an incorrect route further provide a microbial barrier and can prevent related infection. Moreover, attachment of the first non-luer connector 120 to the second non-luer connector 160, or the respective non-luer connections to one another, confirms that the drug in the syringe barrel or other fluid container is applied to the correct route. Further, the attachment of a filter component to the cathether connector and providing a non-luer fitting to the filter component enforces the use of a filter, which can prevent glass shards, microbials or other materials from entering the patient body.

In some applications which require a syringe pump or infusion pump, for example, in continuous delivery applications, in which an extension tubing that is normally used to connect the catheter connector and the syringe or infusion pump, the blunt needle component may be attached to a distal end of the extension tubing and the filter component 140 may be attached to a proximal end of the extension tubing.

A fifth aspect of the present invention pertains to a method of delivering liquid medication to a catheter. In one or more embodiments, the method includes attaching an filter component comprising an inlet, an outlet and filter disposed between the inlet and the outlet to a catheter, providing a blunt needle component comprising including an open distal end, an blunt needle having a lumen in fluid communication with the open distal end, a luer connector attached to the first non-luer connector including an open proximal end in fluid communication with the open distal end and attaching a tip of a syringe barrel to the open proximal end of the blunt needle component. The method further includes filling the syringe barrel with a pre-determined amount of liquid medication and attaching the blunt needle component to the filter component. In one or more specific embodiments, the method utilizes a blunt needle having a length that extends into the inlet and a cross-sectional shape to form a fluid tight connection with the filter component. The method may also utilize a filter component with an inlet having a cross-sectional shape that prevents fluid tight connection with a standard luer connector, IV actuator mechanism and standard syringe barrel.

A sixth aspect of the present invention pertains to an alternative method of delivering liquid medication to a catheter. In one or more embodiments, the method includes providing a blunt needle component including a including an open distal end, an blunt needle extending from the open distal end to a first luer portion, the blunt needle having a length in the range of about 0.1 to about 1.5 inches and a lumen in fluid communication with the open distal end, a second luer portion attached to the first luer portion including an open proximal end in fluid communication with the open distal end. The method also includes providing a filter component including an inlet for receiving the elongate needle, a third luer portion disposed adjacent to the inlet, an outlet and a filter attached to one or both of the inlet and the outlet in fluid communication with the inlet and the outlet. The method further includes adapting the first luer connection portion of the blunt needle component and the third luer connection portion of the filter component to prevent connection to syringe barrels, fluid containers and route-accessing devices that utilize standard luer fittings.

In one or more embodiments, the method includes attaching the blunt needle component to a fluid container containing an amount of a drug to be delivered. In such embodiments, the method includes attaching a luer opening of the fluid container to the second luer connection portion of the blunt needle component. The method also includes attaching the fluid component to a catheter connection. In such embodiments, the method includes attaching the outlet of the filter component to the catheter connection.

Adapting the first luer connection portion of the blunt needle component to prevent connection to syringe barrels, fluid containers and route-accessing devices that utilize standard luer fittings includes attaching a first adapter connector to the blunt needle component, wherein the first adapter connector includes a first open end including a first luer fitting and a second open end including a first non-luer fitting. In such embodiments, the method specifically includes attaching the first luer fitting of the first adapter connector to the first luer connection portion of the blunt needle component. When assembled, the first non-luer fitting of the first adapter connector extends distally from the blunt needle component and is unattached. The first non-luer fitting may include means for preventing connection of the first adapter connector and the blunt needle component to a syringe barrel, fluid container or other route-accessing device which incorporates a standard luer connection or fitting, as described herein.

In one or more embodiments of the method, adapting the third luer connection portion of the filter component to prevent connection to syringe barrels, fluid containers and route-accessing devices that utilize standard luer fittings includes attaching a second adapter connector to the filter component, wherein the second adapter connector includes a third open end including a second luer fitting and a fourth open end including a second non luer fitting. In one or more embodiments, the method specifically includes attaching the second luer fitting of the second adapter connector to the third luer connection portion of the filter component. When assembled, the second non-luer fitting of the second adapter connector extends distally from the filter component and is unattached. The second non-luer fitting may include means for preventing connection of the first adapter connector and the blunt needle component to a syringe barrel, fluid container or other route-accessing device which incorporates a standard luer connection or fitting, as described herein.

When the drug is to be administered, the method includes attaching the first non-luer fitting of the blunt needle component to the second non-luer fitting of the filter component and expelling a predetermined amount of the drug from the fluid container to the blunt needle component, filter component and the catheter connector.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A drug delivery device comprising:
   a blunt needle component including an open distal end, an blunt needle extending from the open distal end to a first non-luer connector, the blunt needle having a length greater than 0.5 inches and a lumen in fluid communication with the open distal end, a luer connector attached to the first non-luer connector including an open proximal end in fluid communication with the open distal end; and
   a filter component including an inlet for receiving the blunt needle, a second non-luer connector disposed adjacent to the inlet for engaging the first non-luer connector, an outlet and a filter attached to one or both of the inlet and the outlet in fluid communication with the inlet and the outlet, the first non-luer connector having a distally extending wall or annular space shaped to prevent attachment of the blunt needle component to an incompatible filter component,
   wherein first non-luer connector and the second non-luer connector are incompatible with standard luer connectors and intravenous route-accessing devices.

2. The drug delivery device of claim 1, wherein the first non-luer connector comprises a collar comprising an inside surface having threads disposed thereon for engaging an outwardly extending rib disposed on the second non-luer connector.

3. The drug delivery device of claim 1, wherein the first non-luer connector comprises an outside surface having threads disposed thereon for engaging corresponding threads disposed on an inside surface of the second non-luer connector.

4. The drug delivery device of claim 1, wherein one or both of the first non-luer connector and the second non-luer connector have cross-sectional widths that are smaller than cross-sectional width of standard luer connectors, intravenous route-accessing devices.

5. The drug delivery device of claim 1, wherein one or both of the first non-luer connector and the second non-luer connector have cross-sectional widths that are larger than cross-sectional widths of standard luer connectors and intravenous route-accessing devices.

6. The drug delivery device of claim 1, wherein the one or both of the first non-luer connector and the second non-luer connector have non-circular cross-sectional shapes.

7. The drug delivery device of claim 1, wherein one or both of the first non-luer connector and the second non-luer connector have connection mechanism selected from an interference fit, snap fit, locking means and combinations thereof.

8. The drug delivery device of claim 1, wherein one or both of the first non-luer connector and the second non-luer connector provide feedback selected from tactile, audible and a combination thereof upon engagement of the first non-luer connector with the second non-luer connector.

9. The drug delivery device of claim 1, wherein one or both of the first non-luer connector and the second non-luer connector is rotatable around the blunt needle.

10. The drug delivery device of claim 1, wherein the blunt needle is non-rigid.

11. The drug delivery device of claim 1, wherein the luer connector includes a permanent attachment element for forming a permanent attachment with an open tip of a syringe barrel.

12. The drug delivery device of claim 1 wherein the outlet comprises a fitting for attaching the filter component to a catheter port.

13. The drug delivery device of claim 12 wherein the outlet includes a permanent attachment element for forming a permanent attachment with the catheter port.

14. The drug delivery device of claim 12, wherein the outlet is rotatable.

15. The drug delivery device of claim 1 wherein the luer connector comprises a luer slip fitting or a luer lock fitting.

16. The drug delivery device of claim 1, wherein the second non-luer connector is incompatible with standard syringe barrels.

17. The drug delivery device of claim 1, wherein the filter is disposed within a housing disposed between the inlet and the outlet.

18. The drug delivery device of claim 1, wherein the filter is disposed in a filter plate attached to one of the inlet and the outlet.

19. The drug delivery device of claim 18, wherein the filter plate includes a first opening for attaching the filter plate to the outlet of the filter component and a second opening for attaching the filter plate to the inlet of the filter component.

20. A drug delivery device comprising:
a blunt needle component including an open distal end, an blunt needle extending from the open distal end to a first non-luer connector, the blunt needle having a length in the range of about 0.5 to about 1.5 inches and a lumen in fluid communication with the open distal end, a luer connector attached to the first non-luer connector including an open proximal end in fluid communication with the open distal end; and
a filter component including an inlet with an opening and a valve for receiving the blunt needle, a second non-luer connector disposed adjacent to the inlet for engaging the first non-luer connector, an outlet and a filter attached to one or both of the inlet and the outlet in fluid communication with the inlet and the outlet,
wherein the valve is configured to open upon application of a force in the distal direction by the blunt needle.

21. The drug delivery device of claim 20, wherein the valve comprises a split septum.

22. The drug delivery device of claim 20, wherein the valve comprises a check valve.

23. The drug delivery device of claim 22, wherein the valve is disposed within the inlet at a distance of at least 0.9 inches from the opening.

24. The drug delivery device of claim 22, wherein the inlet has a cross-sectional shape that is compatible with a cross-sectional shape of the blunt needle.

25. The drug delivery connector of claim 22, wherein the inlet and the blunt needle have a non-circular cross-sectional shape.

26. The drug delivery connector of claim 22, wherein the check valve comprises one of a ball valve and a disc valve.

27. The drug delivery connector of claim 26, wherein the check valve may be spring loaded.

28. A drug delivery device comprising:
a blunt needle component including an open distal end, an blunt needle having a lumen in fluid communication with the open distal end, a luer connector attached to a first connector including an open proximal end in fluid communication with the open distal end; and
an inlet for attaching the blunt needle to a filter component, the blunt needle having a non-luer cross-sectional shape that prevents attachment of a luer connector and IV actuator mechanism to the blunt needle component and permits and blocks fluid communication with the inlet, an outlet and a filter attached to one or both of the inlet and the outlet in fluid communication with the inlet and the outlet, and wherein the first connector comprises a non-luer connector and the filter component comprises a second non-luer connector that prevents attachment of a luer connector, IV actuator mechanism and standard syringe barrel to the inlet.

29. A method of delivering liquid medication to a catheter comprising:
attaching a filter component comprising an inlet, a first non-luer connector integrally connected adjacent to the inlet for engaging a second non-luer connector, an outlet and filter disposed between the inlet and the outlet to a catheter;
providing a blunt needle component comprising including an open distal end, an blunt needle having a lumen in fluid communication with the open distal end, a luer connector attached to a second non-luer connector including an open proximal end in fluid communication with the open distal end;
attaching a tip of a syringe barrel to the open proximal end of the blunt needle component
filling the syringe barrel with a pre-determined amount of liquid medication; and
attaching the blunt needle component to the filter component.

30. The method of claim 29, wherein the blunt needle has a length that extends into the inlet and a cross-sectional shape to form a fluid tight connection with the filter component.

31. The method of claim 29, wherein the inlet has a cross-sectional shape prevents fluid tight connection with a standard luer connector, IV actuator mechanism and standard syringe barrel.

32. A drug delivery device comprising:
a first adapter connector comprising a first open end including a first luer fitting, a second open end including an first non-luer fitting and a first main body having a hollow interior extending from the first open end to the second open end and in fluid communication with the first open end and the second open end; and
a second adapter connector comprising a third open end including a second luer fitting and a fourth open end including a second non-luer fitting, a second main body having a hollow interior extending from the third open end to the fourth open end and in fluid communication with the third open end and the fourth open end,
wherein first non-luer fitting and the second non-luer fitting are incompatible with standard luer fitting and intravenous route-accessing devices.

33. The drug delivery device of claim 32, further comprising;
a blunt needle component including an open distal end, an blunt needle extending from the open distal end to a first luer connection portion, the blunt needle having a length in the range of about 0.1 to about 1.5 inches and a lumen in fluid communication with the open distal end, a second luer connection portion attached to the first luer connection portion including an open proximal end in fluid communication with the open distal end, the first luer connection portion attached to the first luer fitting of the first adapter connector; and a filter component including an inlet for receiving the blunt needle, a third luer connection portion disposed adjacent to the inlet and attached to the second luer fitting of the second adapter connector, an outlet and a filter attached to one or both of the inlet and the outlet in fluid communication with the inlet and the outlet.

34. The drug delivery device of claim 33, wherein the first main body of the first adapter connector comprises a valve for receiving the blunt needle and configured to open upon application of a force in the distal direction by the blunt needle.

35. The drug delivery device of claim 34, wherein the valve comprises a split septum.

36. The drug delivery device of claim 34, wherein the valve comprises a check valve.

* * * * *